(12) United States Patent
Martin et al.

(10) Patent No.: US 10,278,718 B2
(45) Date of Patent: May 7, 2019

(54) FLEXIBLE INTRAVASCULAR TREATMENT DEVICES AND ASSOCIATED SYSTEMS AND METHODS OF USE

(71) Applicant: Covidien LP, Mansfield, MA (US)

(72) Inventors: Brian Martin, Felton, CA (US); Julio Aguilar, Santa Clara, CA (US); Nestor Aganon, San Jose, CA (US); Martin Dieck, Campbell, CA (US)

(73) Assignee: Covidien LP, Mansfield, MA (US)

( * ) Notice: Subject to any disclaimer, the term of this patent is extended or adjusted under 35 U.S.C. 154(b) by 310 days.

(21) Appl. No.: 15/173,343

(22) Filed: Jun. 3, 2016

(65) Prior Publication Data

US 2017/0020542 A1    Jan. 26, 2017

Related U.S. Application Data

(60) Provisional application No. 62/170,581, filed on Jun. 3, 2015.

(51) Int. Cl.
| | |
|---|---|
| *A61M 29/00* | (2006.01) |
| *A61B 17/221* | (2006.01) |
| *A61F 2/88* | (2006.01) |
| *A61F 2/91* | (2013.01) |
| *A61F 2/01* | (2006.01) |
| *A61B 17/00* | (2006.01) |
| *A61B 17/22* | (2006.01) |

(52) U.S. Cl.
CPC ............ *A61B 17/221* (2013.01); *A61F 2/013* (2013.01); *A61F 2/88* (2013.01); *A61F 2/91* (2013.01); *A61B 2017/00867* (2013.01); *A61B 2017/2215* (2013.01); *A61B 2017/22079* (2013.01); *A61F 2002/016* (2013.01); *A61F 2210/0014* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,800,519 | A | * | 9/1998 | Sandock ................... A61F 2/90 606/194 |
| 6,221,100 | B1 | | 4/2001 | Strecker et al. |
| 6,305,436 | B1 | | 10/2001 | Strecker et al. |
| 2005/0110214 | A1 | | 5/2005 | Shank et al. |
| 2015/0018929 | A1 | | 1/2015 | Martin et al. |

OTHER PUBLICATIONS

International Search Report and Written Opinion dated Aug. 23, 2016; International Application No. PCT/US2016/035878; 13 pages.

* cited by examiner

*Primary Examiner* — Melanie R Tyson
(74) *Attorney, Agent, or Firm* — Fortem IP LLP; Mary Fox

(57) ABSTRACT

Flexible expandable treatment devices are disclosed herein. One aspect of the present technology, for example, is directed to an expandable tubular structure formed of an interwoven strand and configured to be positioned in a blood vessel. The interwoven strand may be arranged to form a plurality of cells and a plurality of joints between adjacent cells. At least one of the joints may include a first strand slidably interlocked with a second strand, and at least one of the first strand and the second strand may bend back on itself to form a restriction that limits disengagement of the first strand and the second strand at the joint.

13 Claims, 32 Drawing Sheets

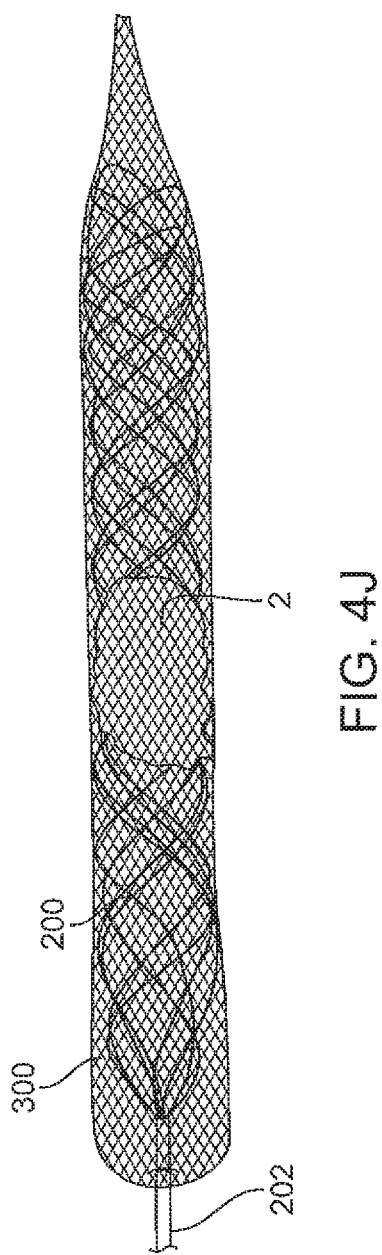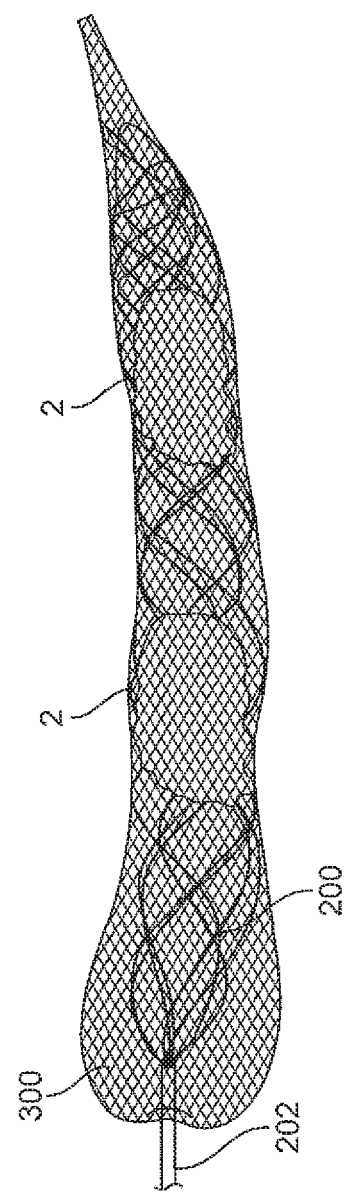

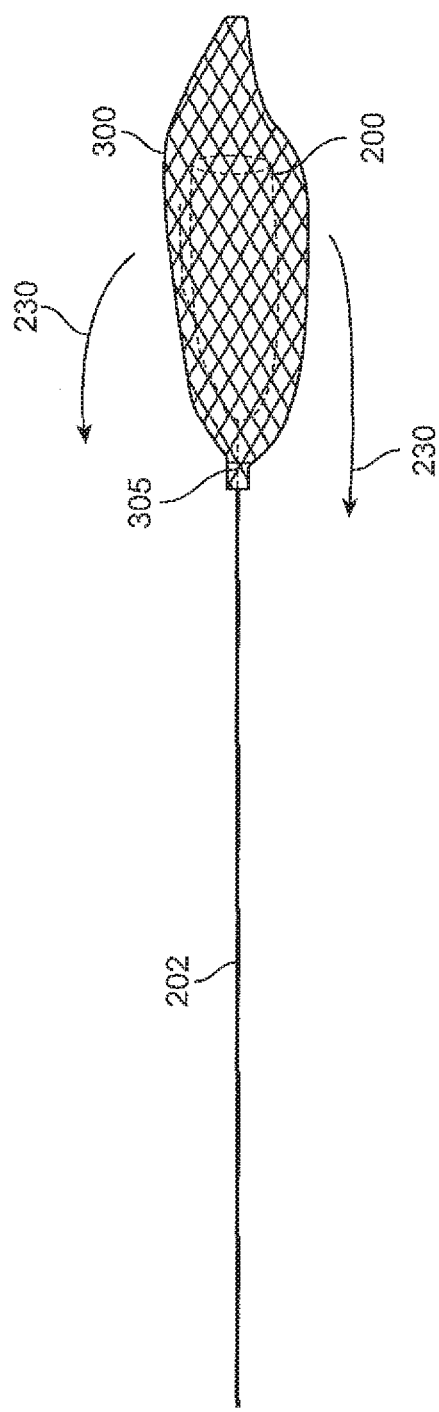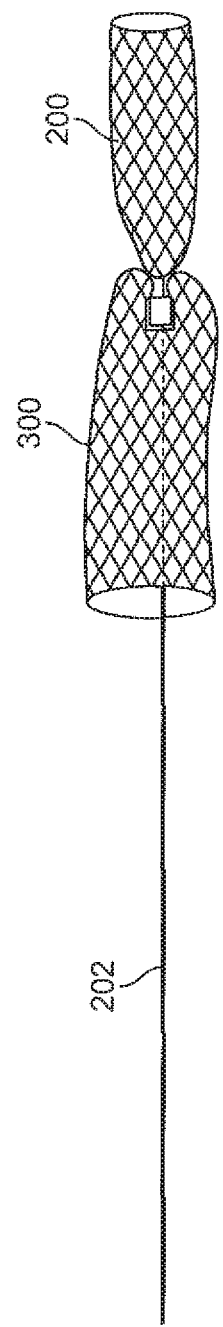
FIG. 5K
FIG. 5L

000
FLEXIBLE INTRAVASCULAR TREATMENT DEVICES AND ASSOCIATED SYSTEMS AND METHODS OF USE

CROSS REFERENCE TO RELATED APPLICATIONS

The present application claims the benefit of U.S. Provisional Application No. 62/170,581, filed Jun. 3, 2015, which is incorporated herein by reference in its entirety.

TECHNICAL FIELD

Disclosed herein are flexible intravascular treatment devices for and associated systems and methods of use. In particular, disclosed herein are flexible devices configured to be positioned within sharp turns of the vasculature.

BACKGROUND

A large number of medical procedures require the use of medical device(s) to remove an obstruction from a body lumen, vessel, or other organ. An inherent risk in such procedures is that mobilizing or otherwise disturbing the obstruction can potentially create further harm if the obstruction or a fragment thereof dislodges from the retrieval device. If a particle or the obstruction breaks free from the device and flows downstream, it is highly likely that the particle or obstruction will become trapped in smaller and more tortuous anatomy. In many cases, the physician will no longer be able to use the same retrieval device to again remove the obstruction because the size of the device may prevent advancing the device to the site of the new obstruction.

Even in successful procedures, a physician must proceed with caution to prevent the walls of the vessel or body lumen from imparting undesired forces to shear or dislodge the obstruction as it is translated through the body during removal. These forces have the potential of breaking portions or fragments of the obstruction away. In some cases, the obstruction can simply break free from the retrieval device and can lodge in a new area causing more concern than the original blockage.

Procedures for restoring flow within the cerebral vasculature as a result of ischemic stroke are one example of where these issues present a concern. The brain relies on its arteries and veins to supply oxygenated blood from the heart and lungs and to remove carbon dioxide and cellular waste from brain tissue. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient. To access the cerebral vasculature, a physician typically advances a catheter from a remote part of the body (typically a leg) through the vasculature and into the cerebral region of the vasculature. Once within the cerebral region, the physician deploys a device for retrieval of the obstruction causing the blockage. Concerns about dislodged obstructions or the migration of dislodged fragments increases the duration of the procedure at time when restoration of blood flow is paramount. Furthermore, a physician might be unaware of one or more fragments that dislodge from the initial obstruction and cause blockage of smaller more distal vessels.

Many physicians currently use stents to perform thrombectomy (i.e. clot removal) to resolve ischemic stroke. Typically, the physician deploys the stent into the clot in an attempt to push the clot to the side of the vessel and re-establish blood to flow. Tissue plasminogen activator ("tPA") is often injected into the bloodstream through an intravenous line. The tPA must travel in the blood stream until it reaches the clot that is causing the blockage. Once the tPA contacts the clot, it begins to break up the clot with the hope of restoring blood flow to the affected areas. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot from the vessel, in a proximal direction, into a guide catheter located within vessels in the patients neck (typically the carotid artery). While this procedure has been shown to be effective in the clinic and easy for the physician to perform, there remain some distinct disadvantages using this approach.

For example, one disadvantage is that the stent may not sufficiently hold onto the clot as it drags the clot to the catheter. In such a case, some or all of the clot might remain the vasculature. Another risk is that use of the stent might mobilize the clot from the original blockage site, but the clot might not adhere to the stent during translation toward the catheter. This is a particular risk when translating through bifurcations and tortuous anatomy. Furthermore, blood flow can migrate the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter. Regardless, simply dragging an expanded stent (either fully or partially expanded) can result in undesired trauma to the vessel. In most cases, since the stent is oversized compared to the vessel, dragging a fixed metallic (or other) structure can pull the arteries and/or strip the cellular lining from the vessel, causing further trauma such as a hemorrhagic stroke (leakage of blood from a cerebral vessel). Also, the stent can become lodged on plaque on the vessel walls resulting in further vascular damage.

In view of the above, there remains a need for improved devices and methods that can remove occlusions from body lumens and/or vessels. While the discussion focuses on applications in the cerebral vasculature, the improved devices and methods described below have applications outside of the area of ischemic stroke.

SUMMARY

An aspect of at least some of the embodiments disclosed herein involves an expandable structure formed of an interwoven strand having a plurality of cells and a plurality of interlocking joints configured to move relative to one another such that the expandable structure, when positioned along a sharp turn in a tubular structure, changes shape to conform to the turn radius at the sharp turn while remaining in apposition with the inner walls of the tubular structure.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 8, 22, 32, 40, 47, 56, 65, or 69. The other clauses can be presented in a similar manner.

1. A medical device comprising:
    an expandable tubular structure formed of an interwoven strand and configured to be positioned in a blood vessel, wherein the interwoven strand is arranged to form a plurality of cells and a plurality of joints between adjacent cells, and
    wherein at least one of the joints includes a first strand slidably interlocked with a second strand, and wherein at least one of the first strand and the second strand bends back on itself to form a restriction that limits disengagement of the first strand and the second strand at the joint.
2. The medical device of Clause 1 wherein the restriction limits longitudinally compressive disengagement of the first strand and the second strand at the joint.
3. The medical device of Clause 1 or Clause 2 wherein the interlocking relationship of the first strand and the second strand limits longitudinally expansive disengagement of the first strand and the second strand at the joint.
4. The medical device of any one of Clauses 1-3 wherein the expandable structure is formed of a single, continuous filament such that both the first strand and the second strand are portions of the same filament.
5. The medical device of any one of Clauses 1-3 wherein the expandable structure is formed of at least a first filament and a second filament separate from the first filament, and wherein the first strand is a portion of the first filament and the second strand is a portion of the second filament.
6. The medical device of any one of Clauses 1-5 wherein:
    the first strand bends back on itself then crosses over itself such that the intersection of the first strand with itself forms a first restriction at the joint, and wherein the bent portion of the first strand and the first restriction together enclose a first opening, and
    the second strand bends back on itself, wherein the bent portion of the second strand extends through the first opening.
7. The medical device of any one of Clauses 1-6 wherein:
    the first strand bends back on itself then crosses over itself such that the intersection of the first strand with itself forms a first restriction at the joint, and wherein the bent portion of the first strand and the first restriction together enclose a first opening, and
    the second strand bends back on itself without crossing over itself, wherein the bent portion of the second strand extends through the first opening.
8. The medical device of any one of Clauses 1-6 wherein:
    the first strand bends back on itself then crosses over itself such that the intersection of the first strand with itself forms a first restriction at the joint, and wherein the bent portion of the first strand and the first restriction together enclose a first opening,
    the second strand bends back on itself then crosses over itself such that the intersection of the second strand with itself forms a second restriction at the joint, and wherein the bent portion of the second strand and the second restriction together enclose a second opening, and
    the bent portion of the second strand extends through the first opening in the first strand.
9. The medical device of any one of Clauses 1-8 wherein both the first strand and the second strand bend back on themselves to form a first restriction and a second restriction at the joint, respectively.
10. The medical device of any one of Clauses 1-5 or 9 wherein:
    the first strand bends back on itself to form a narrowed portion with itself, and the narrowed portion of the first strand forms a first restriction such that the second strand cannot move through the first narrowed portion, and wherein the first strand forms a curved portion that partially encloses a gap, and
    the second strand extends through the gap.
11. The medical device of any one of Clauses 1-5, 9 or 10 wherein:
    the first strand bends back on itself to form a narrowed portion with itself, and the narrowed portion of the first strand forms a first restriction such that the second strand cannot move through the first narrowed portion, and wherein the first strand forms a curved portion that partially encloses a gap, and
    the second strand bends back on itself without crossing over itself, and wherein the second strand extends through the gap.
12. The medical device any one of Clauses 1-5 or 9-11 wherein:
    the first strand bends back on itself to form a narrowed portion with itself, and the narrowed portion of the first strand forms a first restriction such that the second strand cannot move through the first narrowed portion, and wherein the first strand forms a curved portion that partially encloses a first gap;
    the second strand bends back on itself to form a narrowed portion with itself, and the narrowed portion of the second strand forms a second restriction such that the first strand cannot move through the second narrowed portion, and wherein the second strand forms a curved portion that partially encloses a second gap;
    wherein the curved portion of the second strand extends through first gap.
13. The medical device any one of Clauses 1-5 wherein:
    the first strand bends back on itself to form a narrowed portion with itself, and the narrowed portion of the first strand forms a first restriction such that the second strand cannot move through the first narrowed portion, and wherein the first strand forms a curved portion that partially encloses a gap;
    the second strand bends back on itself then crosses over itself such that the intersection of the second strand with itself forms a second restriction at the joint, and wherein the bent portion of the second strand and the second restriction together enclose an opening, and
    the bent portion of the second strand extends through the gap in the first strand.
14. The medical device of any of Clauses 1-5 wherein both the first strand and the second strand bend back on themselves and are arranged in a slip-knot configuration at the joint.
15. A medical device, comprising:
    an expandable tubular structure formed of interconnected strands and configured to be positioned in a blood vessel, wherein the interconnected strands are arranged to form a plurality of cells and a plurality of joints between adjacent cells,
    wherein the interconnected strands include:
        a plurality of first strands each having a first interlocking portion, and
        a plurality of second strands each having a second interlocking portion, wherein at least some of the joints include one of the first interlocking portions slidably coupled to one of the second interlocking portions, and wherein each of the first strand and the second strand bend back on themselves to form first and second restrictions, respectively, and wherein, when the expandable structure is positioned around a tight bend in a blood vessel such that a first length of the expandable structure is under tensile stress and a second length of the expandable structure is under compressive stress, the first and second interlocking portions (1) move away from one another along the length under tensile stress, and (2) move toward one another along the length under compressive stress such that the expandable structure presses outwardly against the vessel wall along the bend and conforms to the curvature of the vessel wall along the bend.

16. The medical device of Clause 15 wherein the restrictions limit the movement of the interlocking portions toward each other along the length.

17. The medical device of Clause 16 wherein the interlocking relationship of the first strands and the second strands at the joints limits movement of the interlocking portions away from each other along the length.

18. The medical device of any one of Clauses 15-17 wherein:

the first strand bends back on itself then crosses over itself such that the intersection of the first strand with itself forms a first restriction at the corresponding joint, and wherein the bent portion of the first strand and the first restriction together enclose a first opening, and wherein the bent portion of the second strand extends through the first opening.

19. The medical device of any one of Clauses 15-18 wherein:

the first strand bends back on itself then crosses over itself such that the intersection of the first strand with itself forms a first restriction at the corresponding joint, and wherein the bent portion of the first strand and the first restriction together enclose a first opening, and the second strand bends back on itself without crossing over itself, wherein the bent portion of the second strand extends through the first opening.

20. The medical device of any one or Clauses 15-18 wherein:

the first strand bends back on itself then crosses over itself such that the intersection of the first strand with itself forms a first restriction at the corresponding joint, and wherein the bent portion of the first strand and the first restriction together enclose a first opening, the second strand bends back on itself then crosses over itself such that the intersection of the second strand with itself forms a second restriction at the corresponding joint, and wherein the bent portion of the second strand and the second restriction together enclose a second opening, and the bent portion of the second strand extends through the first opening in the first strand.

21. The medical device of any one of Clauses 15-17 wherein:

the first strand bends back on itself to form a narrowed portion with itself, and the narrowed portion of the first strand forms a first restriction such that the second interlocking portion cannot move through the first narrowed portion, and wherein the first strand forms a curved portion that partially encloses a gap, and the second strand extends through the gap.

22. The medical device of any one of Clauses 15-17 or 21 wherein:

the first strand bends back on itself to form a narrowed portion with itself, and the narrowed portion of the first strand forms a first restriction such that the second interlocking portion cannot move through the first narrowed portion, and wherein the first strand forms a curved portion that partially encloses a gap, and the second strand bends back on itself without crossing over itself, and wherein the bent portion of the second strand extends through the gap.

23. The medical device of any one of Clauses 15-17, 21 or 22 wherein:

the first strand bends back on itself to form a narrowed portion with itself, and the narrowed portion of the first strand forms a first restriction such that the second interlocking portion cannot move through the first narrowed portion, and wherein the first strand forms a curved portion that partially encloses a first gap, the second strand bends back on itself to form a narrowed portion with itself, and the narrowed portion of the second strand forms a second restriction such that the first interlocking portion cannot move through the second narrowed portion, and wherein the second strand forms a curved portion that partially encloses a second gap, and wherein the curved portion of the second strand extends through first gap.

23. The medical device of Clause 15 wherein the first interlocking portion and the second interlocking portion are arranged in a slip-knot configuration at the corresponding joint.

24. A method for positioning an expandable structure in a bend in a tubular structure, comprising:

positioning an expandable structure in a low-profile state along a bend in a tubular structure, wherein the expandable structure comprises a strand of material interwoven to form a plurality of joints formed of first and second interlocking portions of a first strand and a second strand, respectively;

expanding the expandable structure into apposition with the tubular structure wall along the bend such that the expandable structure conforms to the tubular structure wall;

moving the interlocking portions away from one another along a length of the expandable structure under tensile stress; and moving the first and second interlocking portions toward one another along a length of the expandable structure under compressive stress.

25. The method of Clause 24 wherein the tubular structure is a blood vessel.

26. The method of Clause 24 or Clause 25 wherein the bend is a tight bend.

27. The method of any one of Clauses 24-26 wherein:

both the first strand and the second strand bend back on themselves to form a first restriction and a second restriction at the corresponding joint, respectively, and the method further comprises increasing the distance between the first and second restrictions.

28. The method of any one of Clauses 24-27 wherein:

both the first strand and the second strand bend back on themselves to form a first restriction and a second restriction at the corresponding joint, respectively, and the method further comprises decreasing the distance between the first and second restrictions.

29. The method of any one of Clauses 24-28 wherein:
both the first strand and the second strand bend back on themselves to form a first restriction and a second restriction at the corresponding joint, respectively, and the method further comprises:
increasing the distance between the first and second restrictions, and
decreasing the distance between the first and second restrictions.
30. The method of any one of Clauses 24-29 wherein:
both the first strand and the second strand bend back on themselves to form a first restriction and a second restriction at the corresponding joint, respectively, and
as the expandable structure is expanded in the tight bend, the method further comprises increasing the distance between the first and second restrictions along the length under tensile stress and simultaneously decreasing the distance between the first and second restrictions along the length under compressive stress.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

FIGS. 4J and 4K illustrate examples of an obstruction or other material captured within a retrieval device with a cover further protecting the loaded retrieval device.

FIGS. 5K and 5L show a variation of a cover and retrieval device where the cover is first mounted in a distal direction and then inverted in a proximal direction.

DETAILED DESCRIPTION

It is understood that the examples below discuss uses in the cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

Figure 1:
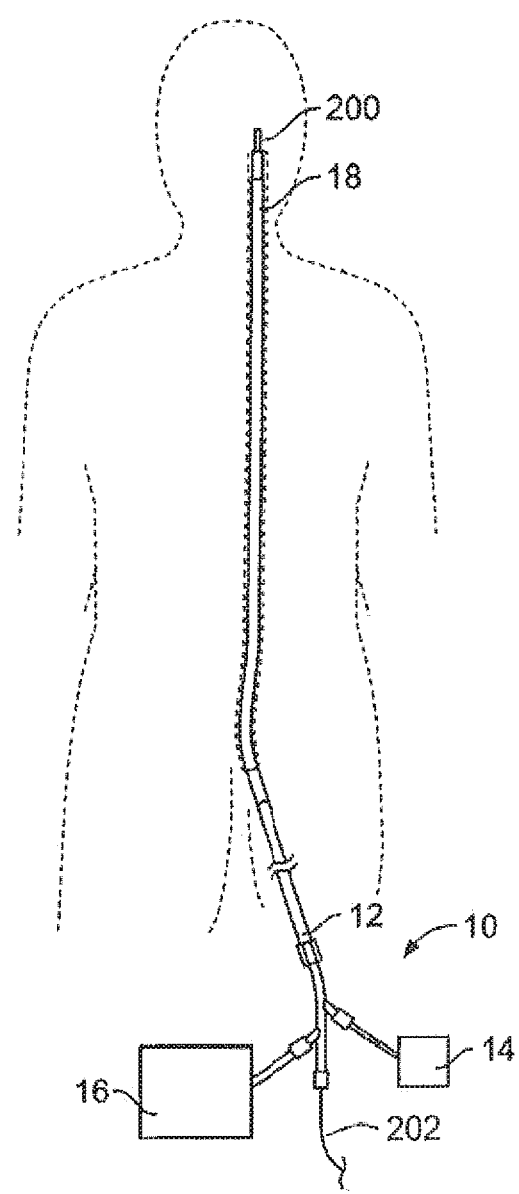
FIG. 1 illustrates an example of a device according to the present invention when used in a system for removing obstructions from body lumens.

FIG. 1 illustrates a system 10 for removing obstructions from body lumens as described herein. In the illustrated example, this variation of the system 10 is suited for removal of an obstruction in the cerebral vasculature. As stated herein, the present devices and methods are useful in other regions of the body including the vasculature and other body lumens or organs. For exemplary purposes, the discussion shall focus on uses of these devices and method in the vasculature.

It is noted that any number of catheters or microcatheters may be used to locate the catheter/microcatheter 12 carrying the obstruction removal device 200 at the desired target site. Such techniques are well understood standard interventional catheterization techniques. Furthermore, the catheter 12 may be coupled to auxiliary or support components 14, 16 (e.g., energy controllers, power supplies, actuators for movement of the device (s), vacuum sources, inflation sources, sources for therapeutic substances, pressure monitoring, flow monitoring, various bio-chemical sensors, biochemical substance, etc.) Again, such components are within the scope of the system described herein.

In addition, devices of the present invention may be packaged in kits including the components discussed above along with guiding catheters, various devices that assist in the stabilization or removal of the obstruction (e.g., proximal-assist devices that holds the proximal end of the obstruction in place preventing it from straying during removal or assisting in the removal of the obstruction), balloon-tipped guide catheters, dilators, etc.

Figure 2A:
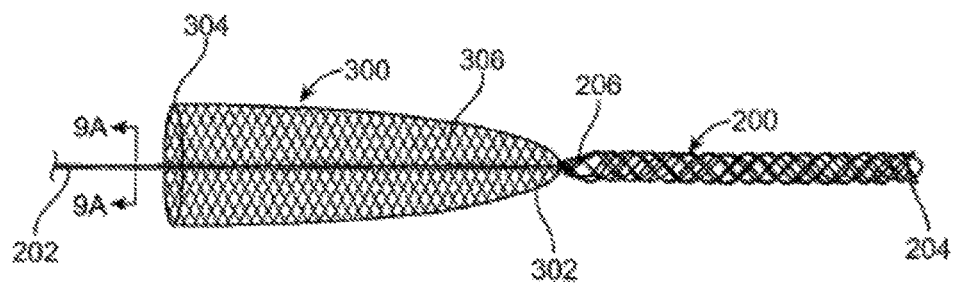
FIGS. 2A to 2C illustrate working ends of various coverable retrieval devices.

FIG. 2A illustrates a working end of a coverable retrieval device 100. Typically, the device includes a capturing or retrieval structure 200. In the illustrated example, the retrieval structure 200 comprises an elongated stent structure. However, unless specifically noted, the capturing structure can comprise any number of devices, including but not limited to a filter, an artherectomy device, a rotational cutter, an aspiration catheter.

The retrieval structure 200 is located at a distal end of a delively wire 202. In one variation, the retrieval structure 200 can be permanently affixed to the delively wire 200 by such methods including, but not limited to adhesive bonding, soldering, welding, polymer joining, or any other conventional method. In some variations, the retrieval device 200 can be formed from one or more wires forming the delivery wire 202 or shaft 202. The delivery wire 202 can have sufficient column strength such that it can axially advance and retract the device 100 within the vasculature as the physician manipulates a non-working end of the delivery wire 202 outside of the body. Accordingly, the delively wire 202 should have a length that is sufficient to extend from the target area, e.g., the cerebral vasculature, to the entry point on the body. Alternatively, additional variations of the device 100 can allow for the use of a support member or catheter that positions the retrieval structure 200 as needed. Additional features of the retrieval structure 200 can be found in the commonly assigned patents and applications cited herein an incorporated by reference.

The coverable retrieval device 100 further includes a cover 300 (also referred to as a funnel or sheath) affixed relative to a proximal end 206 of the retrieval structure 200. By being affixed relative to a proximal end 206, a distal end 204 of the retrieval structure 200 can move relative to the cover 300 so that the cover 300 everts over the proximal end 206 of the structure 200 when the cover 300 is expanded within a vessel and as the structure 200 is withdrawn into the distal end 302 of the cover 300. This mechanism is discussed in detail below.

Figure 2B:
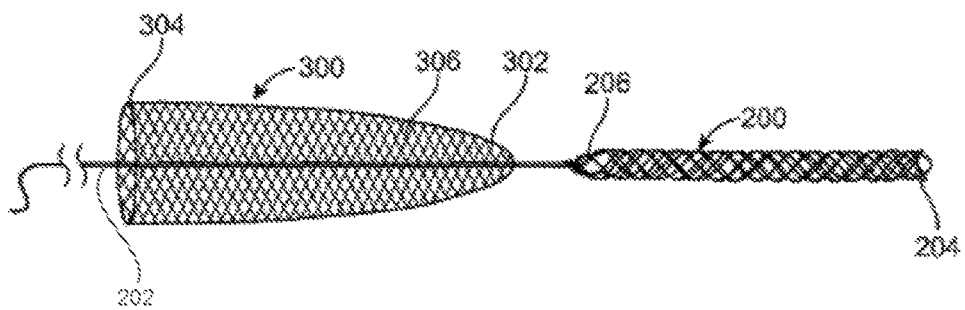
Figure 2C:
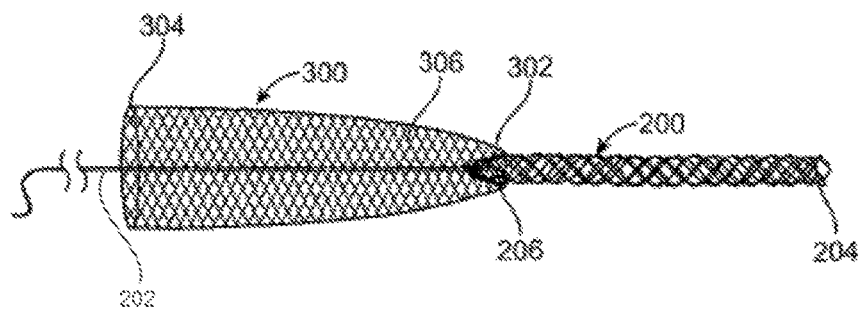

FIGS. 2B and 2C illustrate alternative variations of a coverable retrieval device 100. As shown in FIGS. 2B and 2C, the distal end 302 of the cover 300 can be spaced from the proximal end 206 of the retrieval structure 200. Alternatively, the distal end 302 of the cover 300 can extend over a portion of the retrieval structure 200. In some variations, at least a section of the cover 300 expands to a greater diameter than a diameter of the retrieval structure 200. This allows the cover 300 to expand to a vessel wall where the vessel holds the cover stationary while the device is pulled proximally through the cover to evert the cover. In alternate variations, the cover 300 expands to the same or lesser diameter than the retrieval structure 200 or other device.

Figure 2D:
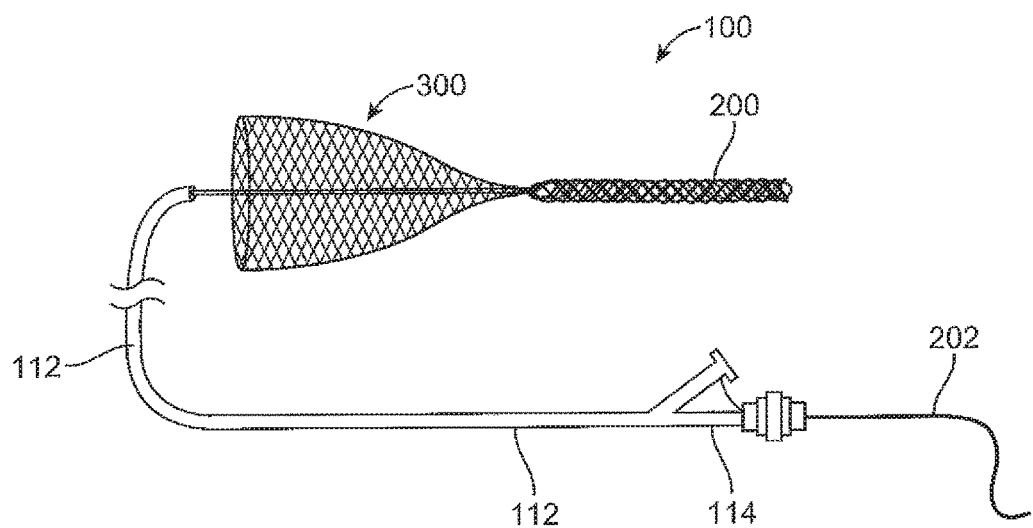
FIGS. 2D and 2E show variations of retrieval devices.

FIG. 2D shows a retrieval device 100 with a catheter 112 (usually a microcatheter). The retrieval device 100 can comprise a single unitary device of a cover 300 and retrieval structure 200 (in this case the retrieval structure is an elongated stent structure). One benefit of a unitary device is that additional devices complicates the procedure and can increase the duration of what is ordinarily a time sensitive procedure. The rehleval device 100 can be positioned through the catheter 112 that includes a hub 114. As a result, the physician only needs to manipulate the unitary retrieval device 100 and the catheter/microcatheter 112. The retrieval device 100 is loaded into the catheter 112 for placement at the target site. In addition, the retrieval device can be reloaded if the procedure must be repeated. The cover 300 and retrieval structure 200 described herein can comprise any construction described herein or as known by those skilled in the art.

Figure 2E:
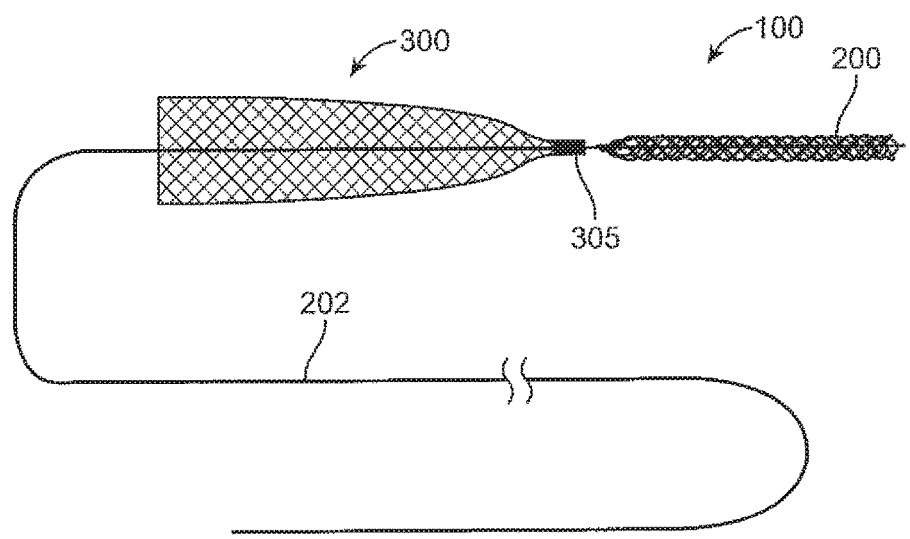

FIG. 2E shows a retrieval device 100 with a cover 300 and retrieval device 200 with a radiopaque marker 305 there between. As shown, variations of the device 100 do not require a catheter or microcatheter.

Figure 2F:
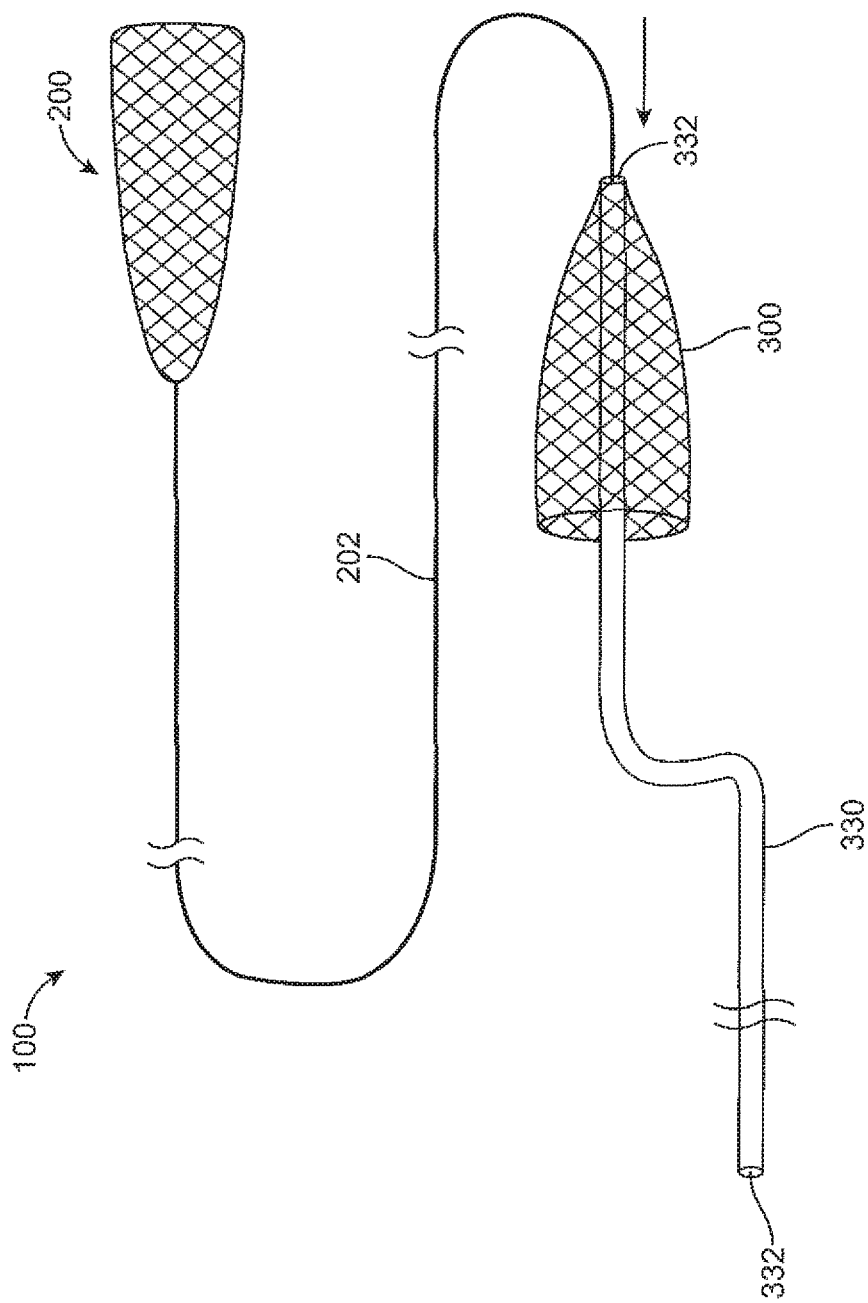
FIG. 2F shows an independent eversible cover on a delivery sheath.

FIG. 2F illustrates an eversible cover 300 located on a sheath 330 having a lumen 332 extending therethrough. A separable retrieval device 200 can be coupled to the cover 300 and sheath 330 by inserting the wire 202 of the cover retrieval device 200 through the lumen 332 of the sheath 330. In this variation, the eversible cover 300 can be used with any number of different interventional tools. The separate devices can be assembled prior to delivery into the patient. Alternatively, the devices can be positioned within the body and subsequently joined once the retrieval device 200 engages the target area.

Figure 3A:
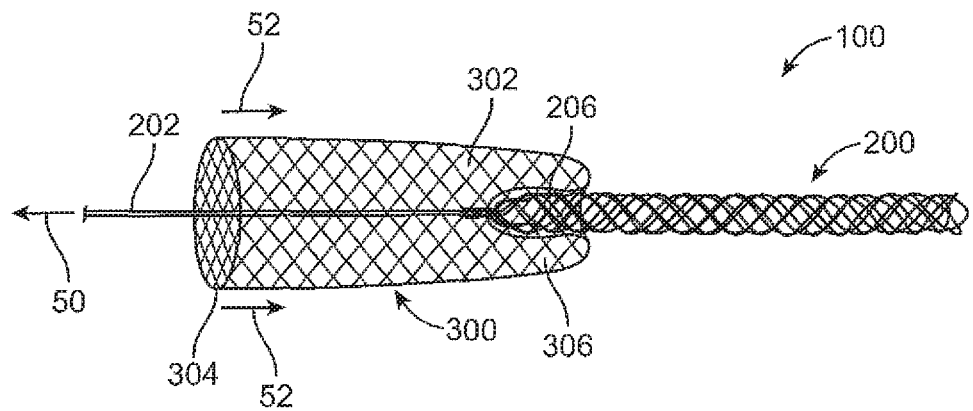
FIGS. 3A to 3C illustrate an example of a coverable retrieval device where the cover everts about the retrieval structure.
Figure 3B:
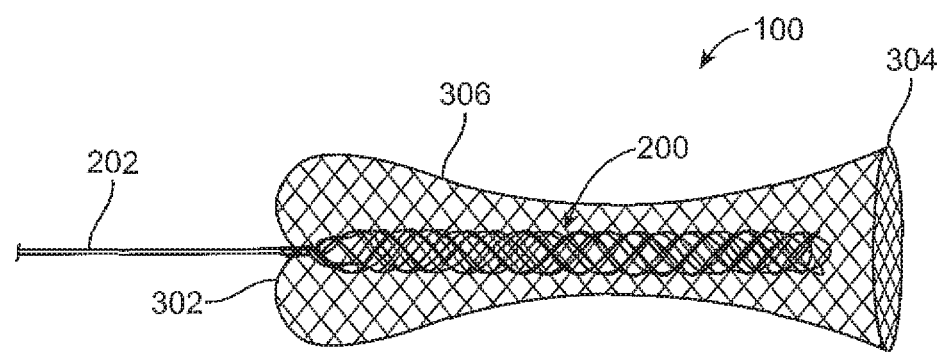

FIG. 3A illustrates an example of a coverable retrieval device 100 where the cover 300 is in the process of everting about the retrieval structure 200. As shown, airnw 50 illustrates a force applied on the wire 202 in a proximal direction. Arrows 52 illustrate a resistance force applied by the friction of the expanded cover 300 against a vessel or similar wall. This friction force 52 prevents or resists proximal movement of the free end 304 of the cover 300 while the fixed end 302 moves in a proximal direction with the proximal end 206 of the retrieval structure 200. This action causes a wall 306 of the cover 300 to evert over the retrieval structure 200. Ultimately, and as shown in FIG. 3B, the free end 304 of the cover 300 ends up distally over the fixed end 302. As shown, the wall of the everted cover 300 provides a safety type cover for the retrieval device 200. In additional variations, the fixed end 302 of the cover can actually be slidable or moveable along the delively wire 202. However, the similar principle as discussed above shall apply to cause everting of the cover 300 over the retrieval structure 200.

Figure 3C:
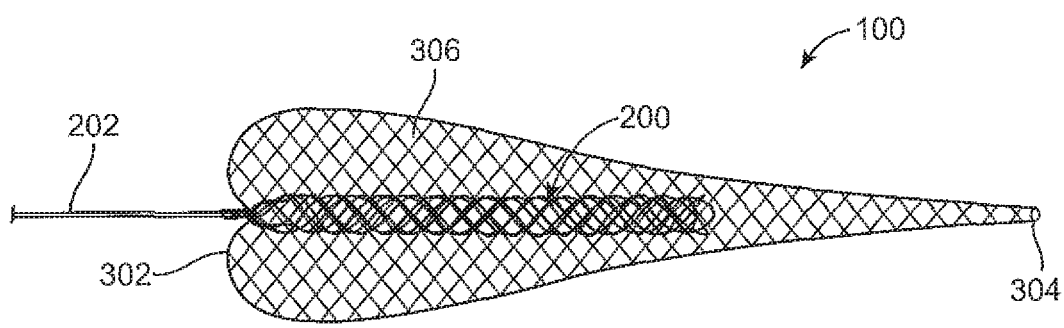

FIG. 3C illustrates another variation of a coverable retrieval device 100 after the cover 300 is everted about the retrieval structure 200. In this variation, the free end 304 of the cover 300 ends up distally of the fixed end 302 and tapers or collapses towards the free end 304. The cover 300 can be shape set so that prior to eversion the cover is as shown above where the forces acting on the cover wall 306 expand outwards, but after eversion the forces on the cover wall 306 cause the tapering or collapsing as shown in FIG. 3C.

In accordance with the illustrations discussed above, the cover 300 can be made so that the cover wall 306 is atraumatic when dragged across a lumen wall. The cover can be manufactured from any number of materials including a fabric, a reinforced fabric, a braid, weave, or any such material that allows for expansion against a wall of the body lumen or vessel as well as to allow everting of a wall 306 of the cover over the retrieval device 200. The cover wall 306 can also comprise combinations of these materials such as braids of polymer material with metal fibers, soft braids with coil reinforcements or various other combinations.

The cover wall can comprise a mesh that can include any medically acceptable materials such as a Nitinol braid. Furthermore, the mesh allows for flow through the vessel or lumen while expanded. However, additional variations of the device can include a solid layer of material substituted for the mesh. Moreover the cover can comprise any number of configurations. For example, the cover can comprise a single layer wall or a multi-layer wall, the open end of the cover could be made to have terminated ends such as by using continuous wire loops fanned during the braiding process. Alternatively, the ends can be cut and then terminated by encasing in polymer, laser welds, or by folding inward for a discrete length and then terminating In one example, the cover 300 comprises a continuous wire construction as described in earlier commonly assigned patent applications incorporated by reference. In one variation the cover 300 comprises a finely braided wire, such as 48-96 wires of 0.0005" to 0.002" diameter fine Nitinol wire or similar. Additionally, the wire can comprise cobalt chromium, stainless steel, or similar, or drawn filled tube (DFT) with platinum core. In additional variations, a flat wire or oval wire can be used. The wire does not need to be uniform. Instead, a number of different types of wires can be used. Some of the individual wires could be platinum alloys for added radiopacity.

Figure 4A:
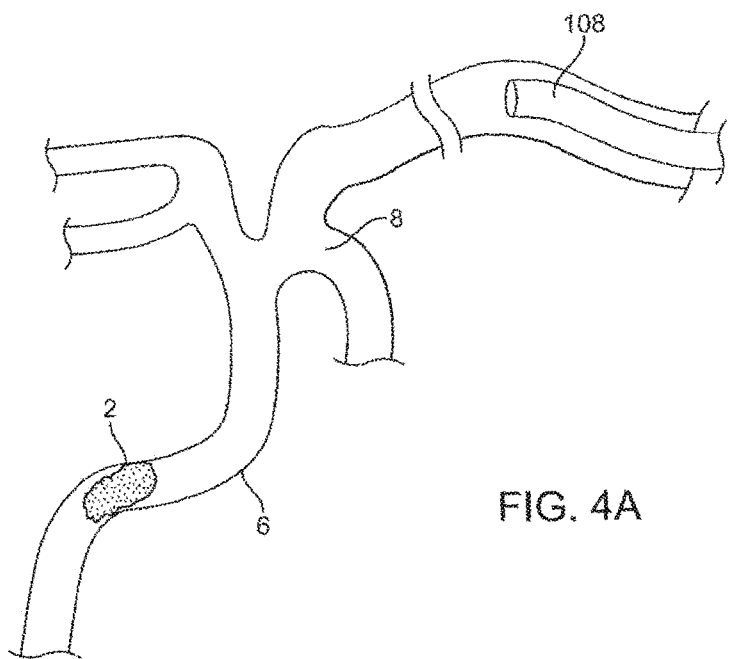
FIG. 4A to 4I illustrates an example where an improved retrieval device with passive protection retrieves a clot from tortuous anatomy.

FIG. 4A to 4I illustrates an example where an improved retrieval device 100 with passive protection retrieves a clot 2 from tortuous anatomy. FIG. 4A illustrates a clot 2 that obstructs blood flow in a vessel 6. As noted herein, the vessel 6 can comprise any vessel in cerebral vasculature, coronary or peripheral vasculature. Alternatively, the device and methods for use are not limited to use in the vasculature. Variations of the principles, concepts, method and devices described herein can be applicable wherever a retrieval device can be used. FIG. 4A also illustrates a guide sheath or access catheter 108 that is advanced within the vessel. During a procedure, the physician will advance the access catheter 108 as far distally as possible. However, due to the size of the access catheter 108, a physician typically positions it a distance away from the obstruction 2. As shown, there can be any number of bifurcations 8 in the vessel 6 located between the access catheter 108 and the obstruction 2. As discussed herein, in some variations, the access catheter 108 can be used to remove the obstruction 2 from the body once the obstruction is captured by a retrieval device. However, the greater the distance between the initial location of the obstruction 2 and the location of the access catheter 108, the greater the risk that the obstruction 2 can break free from the retrieval device or become dislodged due to anatomic or environmental features, including but not limited to bifurcations, the wall of the lumen, the tortuosity of the anatomy, vessel wall plaque, etc.

Figure 4B:
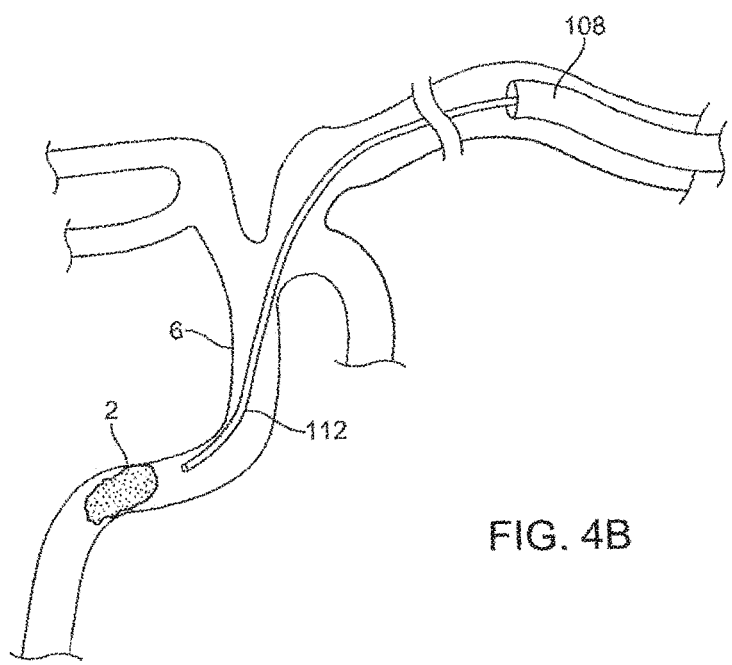
Figure 4C:
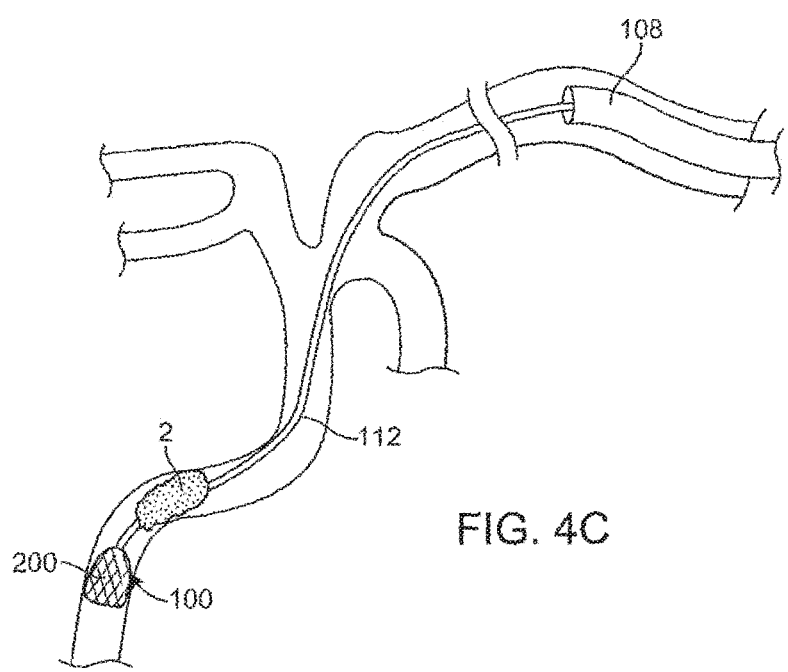
Figure 4D:
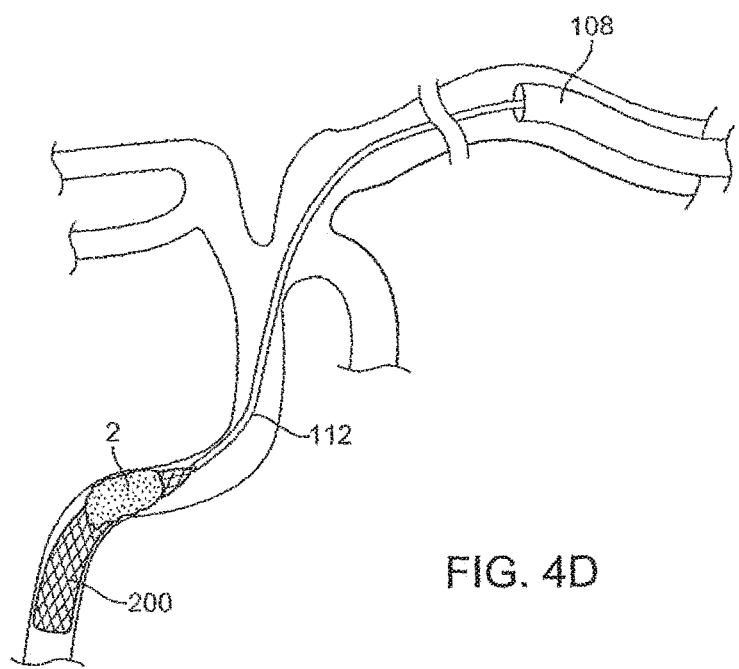

FIG. 4B illustrates an optional catheter 112 that advances from the access catheter 108 to the site of the obstruction 2. Once at the site, the catheter 112 can deploy a retrieval device (not shown in FIG. 4B) so that the retrieval device can engage the clot 2. Alternatively, the catheter 112 can traverse the obstruction 2 as shown in FIG. 4C and deploy a portion of the retrieval device 100 distally to the obstruction 2. The physician then manipulates the retrieval device 100 to secure the obstruction 2. For example, the physician can deploy the retrieval structure 200 distally to the obstruction 6 and withdraw the retrieval structure 200 proximally to secure the obstruction 2. In another variation, the physician can position the retrieval structure 200 within the catheter 2 while the catheter 112 is through or adjacent to the obstruction 2. Then, the physician can withdraw the catheter 112 to expose the retrieval structure 200 so that it secures to the obstruction 2 after expansion. In the illustrated example, the retrieval structure 200 comprises an elongated stent type structure that expands (or is expanded) to enmesh or secure to the obstruction. Although not illustrated, the system can include a distal capture filter or basket as described in any of the commonly assigned applications incorporated by reference herein.

Figure 4E:
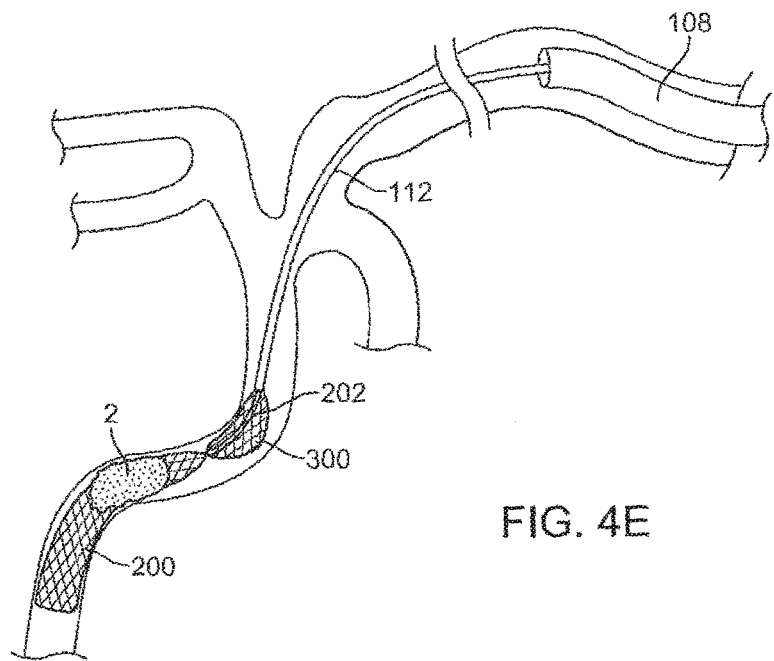

Next, as shown in FIG. 4E, the physician can further withdraw the catheter 112 to expose a cover 300 as described above. In many cases, the physician exposes the cove 300 once the retrieval structure 200 is engaged with the obstruction 2. This sequential process allows for easier repositioning of the retrieval structure 200 if necessary. Alternatively, the cover 300 can be deployed plior to engaging the retrieval structure 200 with the obstruction 2. If necessary, the physician can apply a proximal force on the delivery wire 202 while withdrawing the catheter 112 to prevent inadvertent movement of the obstruction 2 and retrieval device 200.

Figure 4F:
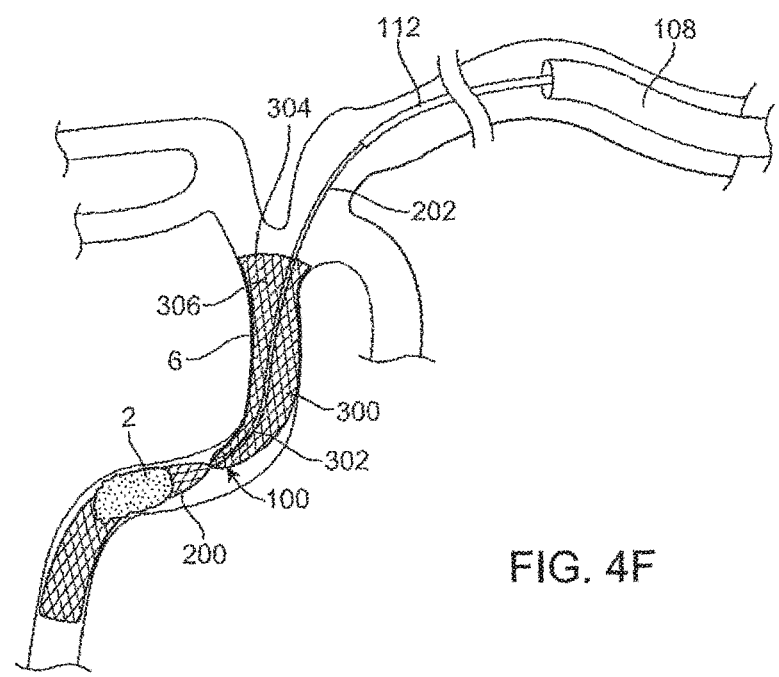

FIG. 4F illustrates the stage with a fully exposed the cover 300 and a catheter 112 moved closer towards the access sheath 108. As shown, the free end 304 of the cover 300 is proximal to fixed end 302 of the cover 300. As also noted above, the cover 300 can be a shape memoly alloy that expands against the walls of the vessel 6 upon reaching body temperature. Alternatively, the cover 300 can be self-expanding upon deployment into the vessel 6. In some variations, the cover wall 306 comprises a porous material or construction that allows blood to continue to flow through the cover 300.

In addition, some variations of the retrieval device 100 include a cover 300 that has at least a section that expands to a greater diameter or dimension than the retrieval structure 200. This allows for expansion of the cover 300 against the wall of the vessel 6. In most variation, expansion of the cover 300 provides sufficient friction against the walls of the vessel to overcome column strength of the cover walls 306 allowing for everting of the cover walls 306 over the retrieval structure 200 and obstruction 2 as discussed herein. As noted above, in alternate variations the cover 300 can expand a diameter or dimension that is equal to or less than the retrieval structure 200.

Figure 4G:
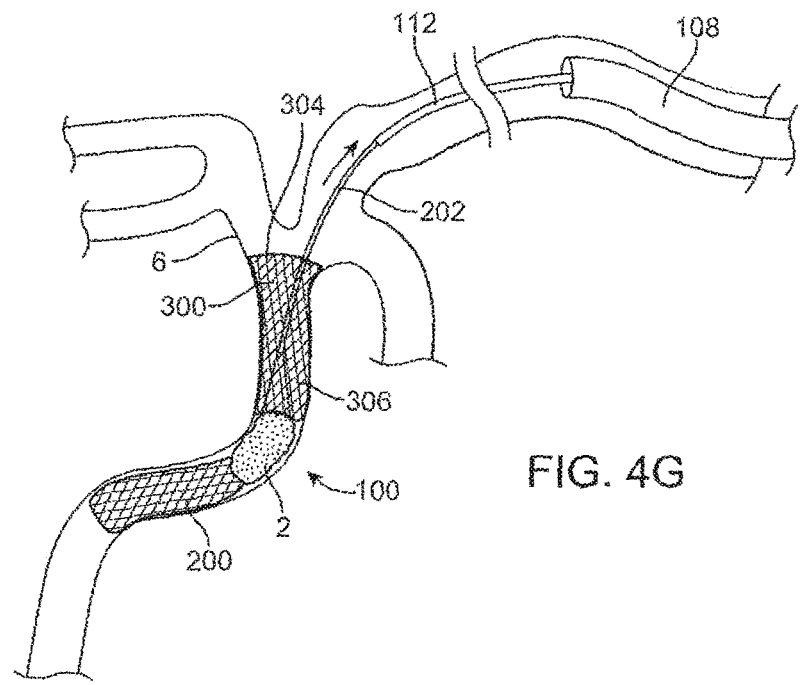

FIG. 4G illustrates proximal movement of the delively wire 202, which causes proximal translation of the obstruction 2 and retrieval structure 200. Because the cover 300 is expanded against the walls of the vessel 6 the free end 304 of the cover 300 does not move or moves less than the fixed end 306 of the cover 300. The fixed end 306 moves with the obstruction 2 and retrieval structure 200 in a proximal direction causing the cover walls 306 to evert over the obstruction 2 and retrieval structure 200. Unlike a conventional funnel, the everting cover functions similar to a conveyor belt type movement as the obstruction and retrieval structure move together. This action allows for a passive type of protection since cover 300 does not need to be actuated over the obstruction 2 and retrieval structure 200 and can be performed in a quick manner by simply withdrawing the deployed retrieval device 100.

Figure 4H:
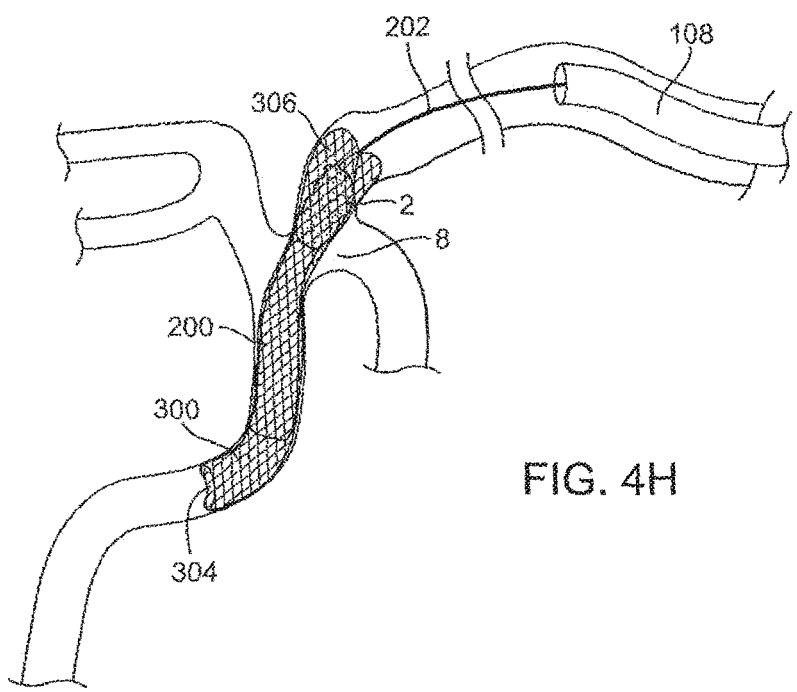

FIG. 4H illustrates a stage where the fixed end 306 of the cover 300 is now proximal to the free end 304. As shown, the everted cover 300 forms a protective sheath or cover over the obstruction 2 and the retrieval structure 200. FIG. 4H also illustrates how the cover 300 protects the obstruction 2 and retrieval structure 200 as they are pulled along the vessel and navigate the tortuous anatomy, walls of the vessel, as well as bifurcations 8. The cover 300 and cover wall 306 also protects the vasculature from the surface of the retrieval structure 200 and obstruction 2.

Figure 4I:
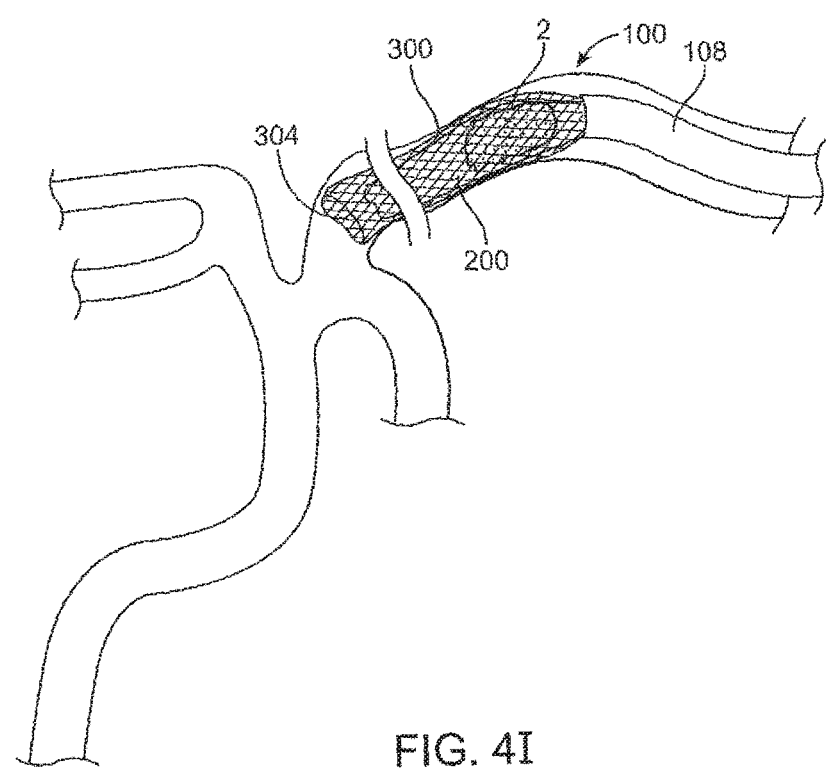

FIG. 4I shows the obstruction 2 and retrieval structure 200 protected by the cover 300 as the retrieval device 100 is positioned against or within the access catheter 108 in preparation for removal from the body. The retrieval device 100 can remain outside of the access catheter 108 as the physician removes both devices from the body. Alternatively, the cover 300 can assist in pulling the retrieval device 100 and obstruction 2 into the access catheter 108 by compressing the obstruction 2 as it is pulled into the access catheter 108.

FIGS. 4J and 4K illustrate examples of an obstruction or other material 2 captured within a retrieval device 2 with a cover 300 further protecting the loaded retrieval device 200.

Figure 5A:
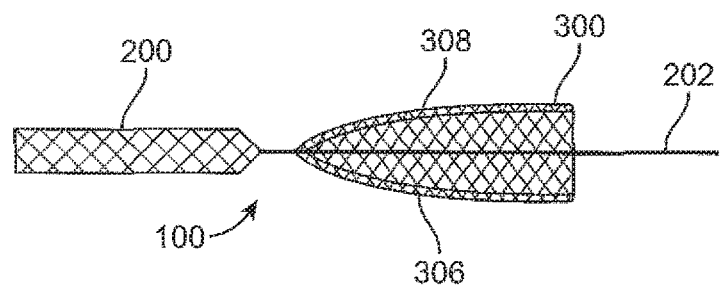
FIG. 5A illustrates a retrieval device having a retrieval structure adjacent to a double layer cover.

FIGS. 5A to 5K show a variety of cover configurations. FIG. 5A illustrates a retrieval device 100 having a retrieval structure 200 adjacent to a double layer cover 300 with an exterior wall 306 and an interior wall 308.

Figure 5B:
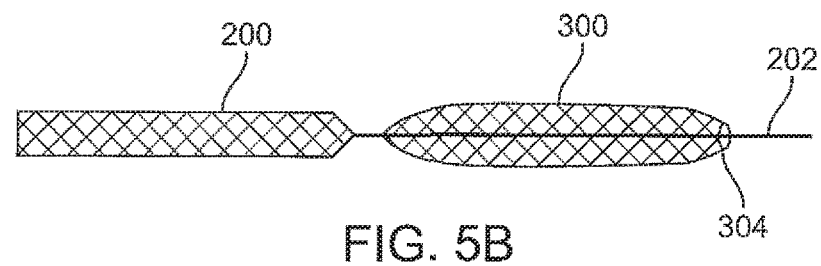
FIG. 5B shows a funnel with a free end that tapers down about the delively wire.

FIG. 5B shows a cover 300 with a free end 304 that tapers down about the delivery wire 202 where the cover 300 will eventually form a double wall configuration when the cover 300 everts over the retrieval structure 200. The tapered free end 304 limits the cover 304 from moving once the retrieval structure 200 reaches the free end 304 thereby forming double wall protection over the retrieval structure 200.

Figure 5C:
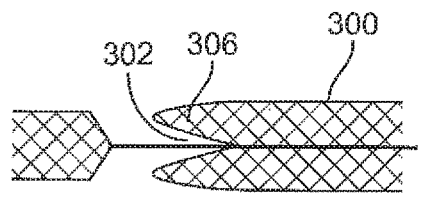
FIGS. 5C and 5D show a fixed end of a cover that is pre-shaped to reduce the force required to evert the cover wall.
Figure 5D:
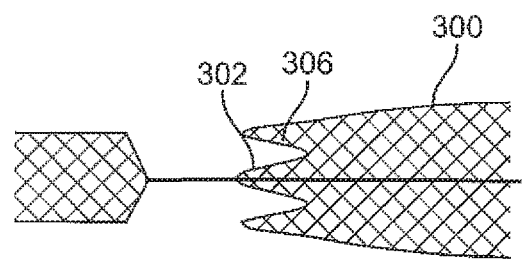

FIGS. 5C and 5D show how a fixed end 302 of a cover 300 can be pre-shaped to reduce the force required to evert the cover wall 306 or to lower the threshold to trigger passive covering of the retrieval structure by the cover.

Figure 5E:
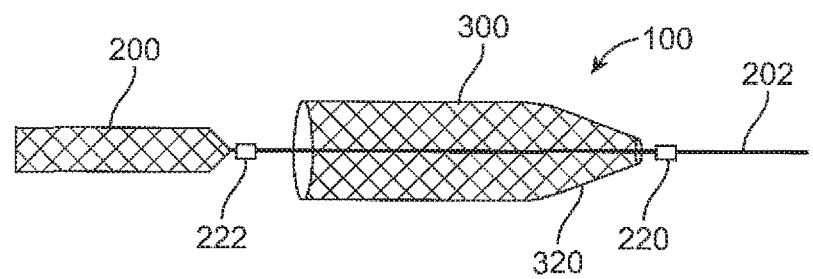
FIG. 5E shows alternate variation of a passive cover integrated into a retrieval device.

FIG. 5E shows alternate variation of a passive cover 300 integrated into a retrieval device 100. In this variation, the retrieval device 100 includes a control shaft or wire 202 to manipulate the working end of the retrieval device 100. The cover 300 floats along the shaft 202 between two fixed anchors or nodes 220, 222. The cover 300 can float or slide between the fixed nodes 220, 222. The nodes 220, 222 can comprise radiopaque marker bands, glue joints, or any other mechanical obstructions capable of stopping the translation of cover 300. When the device 100 advances through a microcatheter, the rear or proximal node 220 limits rearward movement of the cover 300. When positioned appropriately, the microcatheter can be withdrawn to expose the retrieval device 200 and cover 300 as described herein. When the retrieval structure 200 engages the obstruction (not shown) the retrieval device 100 can be withdrawn by pulling on the delively shaft 202. While this occurs, the cover 300, being expanded against the vessel remains stationary (or moves at a slower rate than the obstruction and retrieval structure 200 due to the friction against the vessel wall). The retrieval structure 200 and clot enter the cover 300, causing the distal node 222 to make contact with the near end 320 of the cover 300. This contact causes the retrieval structure 200 and cover 300 to translate as an integrated unit. It should be appreciated that the cover could be a single layer or double layer cover, and could have any of the wire design variables and termination variables described herein.

Figure 5F:
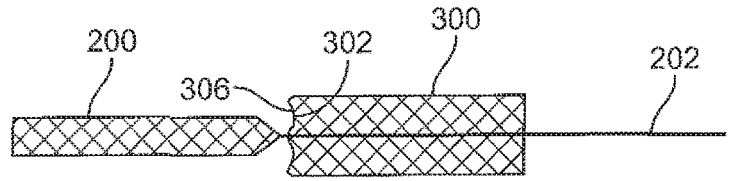
FIG. 5F illustrates a cover having a pre-set flattened cover wall at a fixed end of the retrieval structure.
Figure 5G:
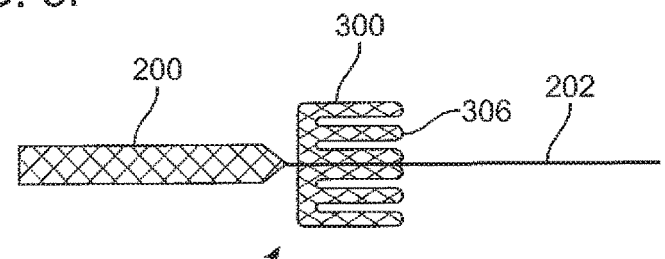
FIGS. 5G to 5I illustrate various layered covers.
Figure 5H:
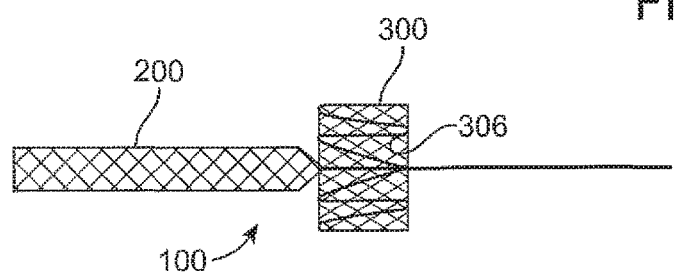
Figure 5I:
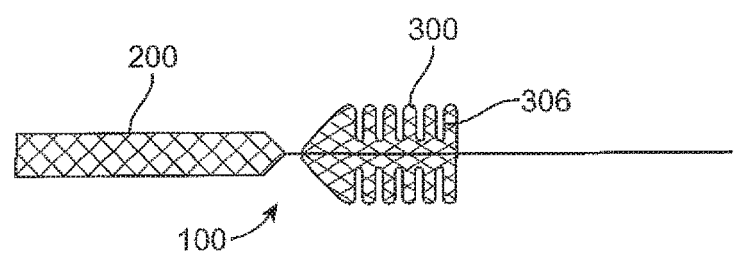

FIG. 5F illustrates a cover having a pre-set flattened cover wall 304 at a fixed end 302 that is spaced from a proximal end of the retrieval structure 200. FIGS. 5G to 5I illustrate various layered covers 300. The layered covers allow for shortening the axial length of the cover and therefore shortens the required translation length. Layering of the cover wall 306 allows for a shortened deployed length of the cover 300 when deployed in the vessel or body structure. As the cover 300 everts over the retrieval structure 200 the layered wall 306 extends. As a result, shortening the length reduces the length that the cover 300 extends into the proximal vessels and reduces the length of that the retrieval structure 200 must travel to become protected by the cover 300. This also helps shorten the distance required to move the device 100 to complete eversion of the cover 300.

Figure 5J:
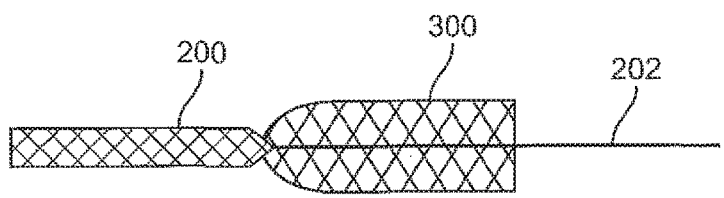
FIG. 5J shows a cover that is constructed directly onto the retrieval structure rather than the delivery shaft.

FIG. 5J shows a cover 300 that is constructed directly onto the retrieval structure 200 rather than the delivery shaft 202. This construction also assists in reducing the distance necessary to complete passive protection of the retrieval structure by the cover.

FIG. 5K show a variation of a cover 300 that is mounted in a distal direction over the retrieval device 200 and then everted in a proximal direction over the wires or shaft 202 as shown by arrows 230. Once everted, as shown by FIG. 5L, the device 100 is ready for deployment as discussed herein.

Figure 6A:
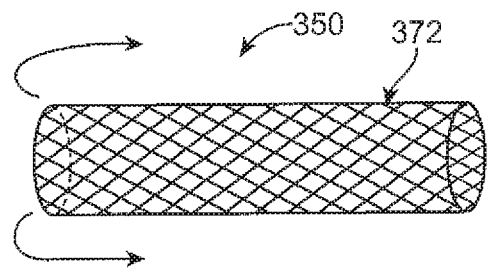
FIGS. 6A to 6L illustrate a variation of covers for use as describe herein.
Figure 6B:
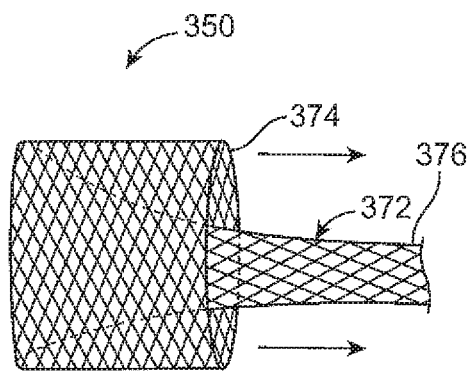

FIGS. 6A and 6B illustrate a variation of a cover 350 for use as described herein. Additionally, the cover 350 can be used with any obstruction retrieval device not limited to the retrieval baskets and stents described herein. The covers 350 disclosed herein can be used where the physician desires to shield the obstruction being removed from the frictional effects of the arteries or from the local anatomy (e.g., branching vessels, tortuous anatomy, or other substances on the vessel walls). In use, the covers can be sized for use with guide catheters, micro-catheters, and/or distal access catheters. The covers can include any number of radiopaque marker bands to allow non-invasive imaging of the device (see marker 390 affixed between cover 350 and shaft 212 in FIG. 7B as one example). In any case, once the retrieval device captures a clot or obstruction, as described above, the device and clot are protected by the cover so that the cover eliminates or reduces direct contact between the interior of the wall of the vessel and the clot.

Figure 6C:
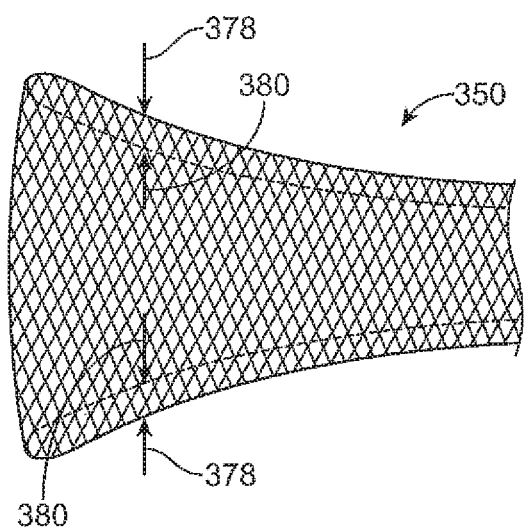
Figure 6D:
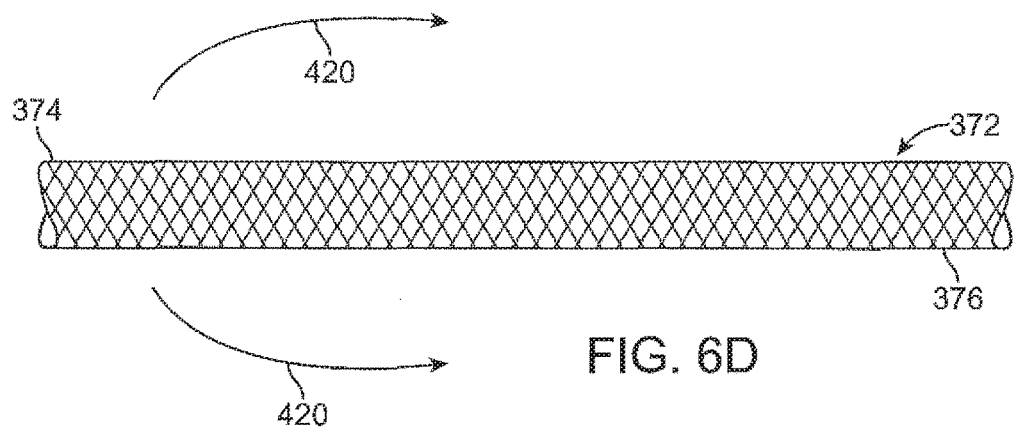

FIGS. 6A to 6C show a variation in which a cover is created from one or more mesh tubes 372. FIG. 6B illustrates inversion of the tube 372 so that a first end 374 is drawn over the tube 372 towards a second end 376. As shown in FIG. 6C, this creates a double walled cover having an exterior wall 378 separated from an interior wall 380. In one example, such a spacing or gap could range between 0.001 inches to 0.100 inches. However, any range is contemplated within alternative variations of the device. In some variations the inverted cover 350 is heat set to maintain a separation between layers or walls 378 380 of the cover 350. Typically, if the cover 350 is not created from a radiopaque material, a marker band will be placed on the proximal end 376 and adjacent to a shaft or catheter to which the cover 350 is attached. In some variations the construction of the mesh material is compliant to allow for movement of a first part of the mesh relative to a second part of the mesh through compression and expansion of the mesh material. In such a case, the individual strands forming the mesh are moveable relative to one another to cause the mesh to be naturally compliant. Accordingly, this construction permits the inner wall 380 to move or deflect with the retrieval device and/or obstruction as the device is withdrawn into the cover 350. In some variations, both ends of the mesh 374 and 376 are affixed to the catheter, shaft or wire.

In many variations, the cover mesh is selected to minimize friction when the interior layer 380 moves against the exterior layer 378. For example, the braid pattern, wire, wire diameter, angle of the braid and or other features can be selected to reduce friction between the outer layer 378 and inner layer 380. This permits the inner layer 380 to move proximally with a retrieval device while the outer layer remains stationary. Again, as discussed above, the construction of the mesh permits compression and expansion of the mesh layer to permit movement of the inner layer while the outer layer remains affixed when engaged against the vessel wall. In certain variations, the cover is heat set so that the inner layer has cushioning and the ability to deflect to assist in movement of the inner layer. FIG. 5C also illustrates a cover 350 having a tapered design.

Figure 6E:
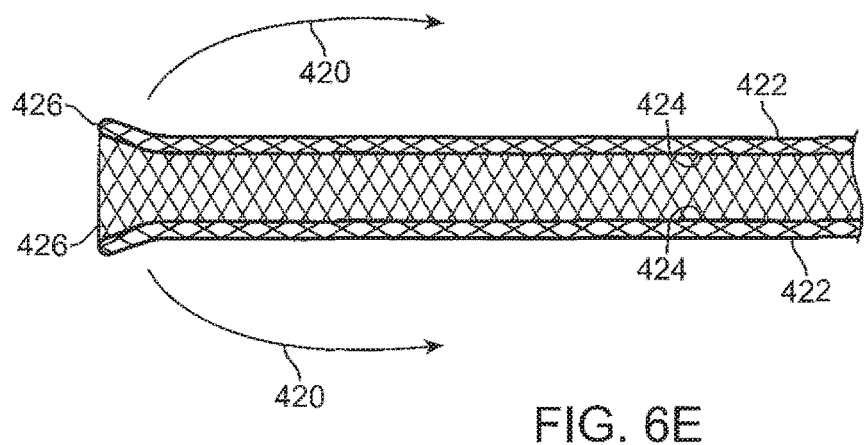
Figure 6F:
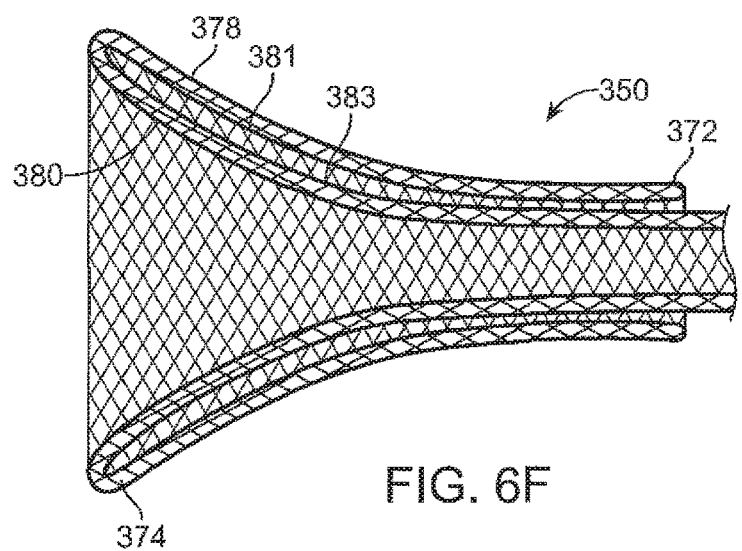

FIGS. 6D to 6L illustrate additional variations of cover construction to produce covers having more than two walls. For example, a mesh tube 372 is everted or drawn over a second end 376 in the direction 420. As shown in FIG. 6E this produces a dual layer cover having open ends 422 and 424 and a folded end 426. The dual layer tube is then folded over again in the direction 420. This creates a cover construction with an exterior layer 378 and an interior layer 380 as well as a first intermediate layer 381 and a second intermediate layer 383. As shown in FIG. 6F, the cover can be set to assume the tapered shape having an opening at the first end 374 that is flared with the ends of the mesh at the second end 372, which are ultimately affixed to a shaft, wire or other catheter device as described herein.

Figure 6G:
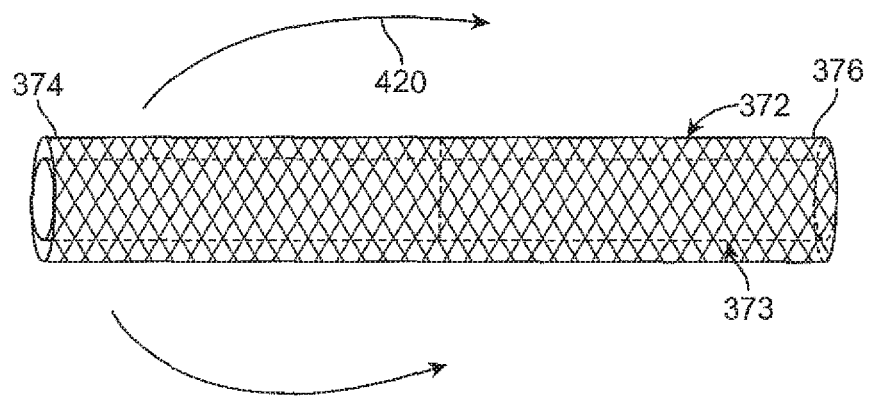
Figure 6H:
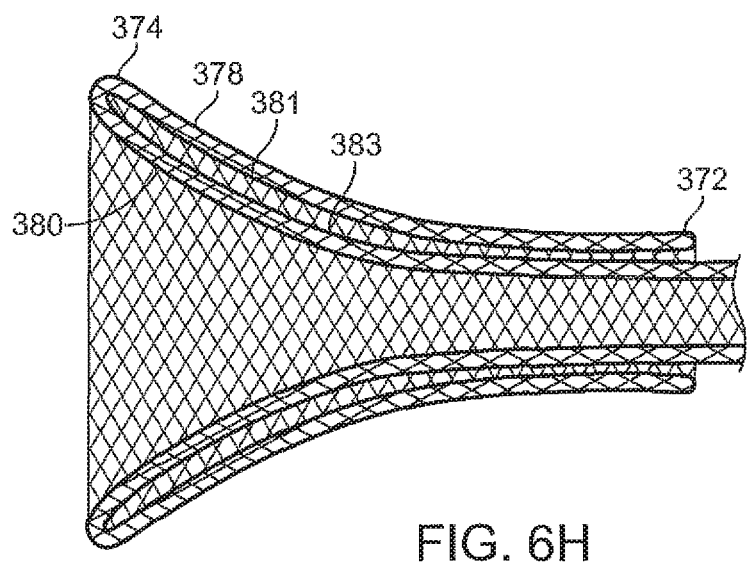

FIG. 6G illustrates another example of a cover construction. As shown, a first mesh tube 372 is placed coaxially with a second tube 372. The concentric tubes are then everted in direction 420 to produce a four layer cover. As shown in FIG. 6H, the cover can comprise an interior mesh layer 380, and exterior mesh layer 378 as well as any number of intermediate layers 381, 383 depending on the number of tubes that are initially used. The second end 372 of the cover 350 includes four unconnected ends of the mesh tubes that can be affixed to a shaft or tube as discussed herein, while the first end 374 of the cover 350 can be shape set to taper from the opening.

Figure 6I:
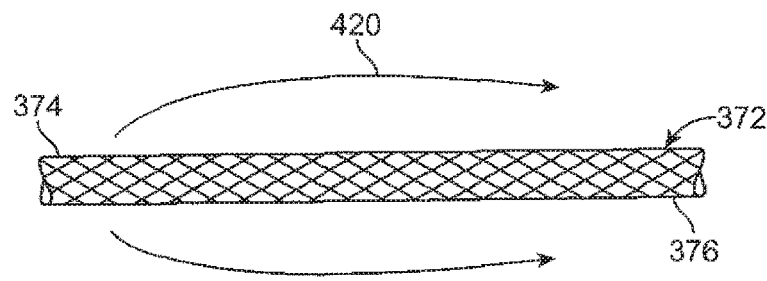
Figure 6J:
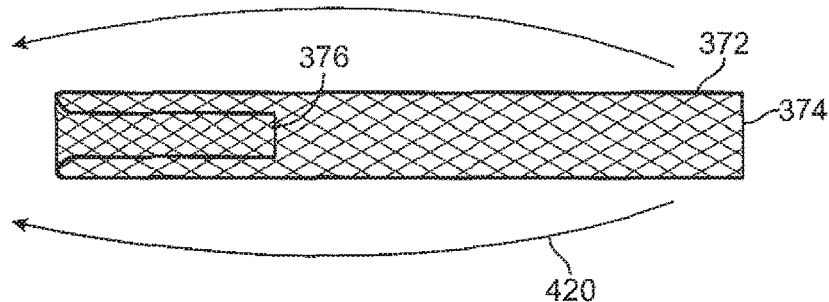
Figure 6K:
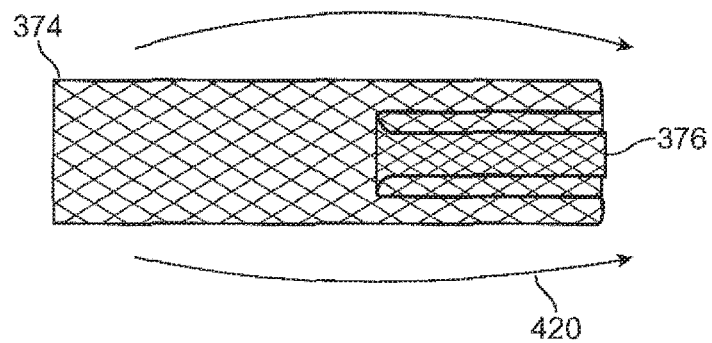
Figure 6L:
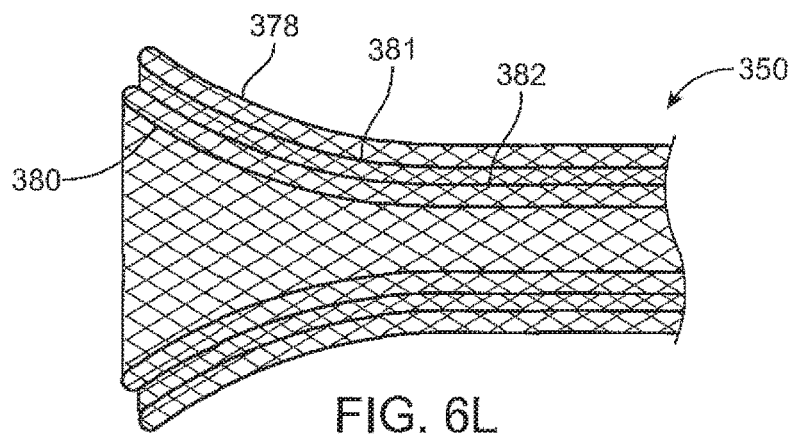

FIGS. 6I to 6L illustrate another example of the construction of a multi-wall cover. As shown in FIG. 6I, a first end 374 of a mesh tube 372 is everted over and beyond a second 376 in direction 420 to produce the configuration of FIG. 6J. Next, the first end 374 is everted or folded back in direction 420 to produce the configuration of FIG. 6K. Finally, the first end 374 is folded again in direction 420 so that the ends 374 and 376 are even to produce the cover configuration shown in FIG. 6K. Again, one end of the cover 350 can be set to form the tapered shape while the other respective end can be affixed to a catheter or shaft.

Although the covers of the present disclosure are presented without additional structures, it should be noted that these covers are coupled with a shaft or other member so that the cover can be advanced within the target anatomy to assist in removal of a device, structure, or debris from the site.

Figure 7A:
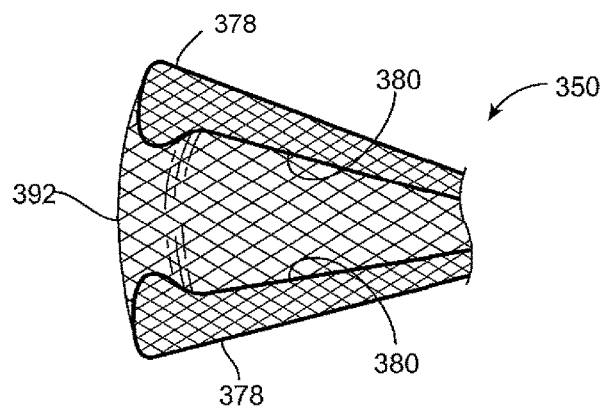
FIGS. 7A to 7C show additional variations of covers.
Figure 7B:
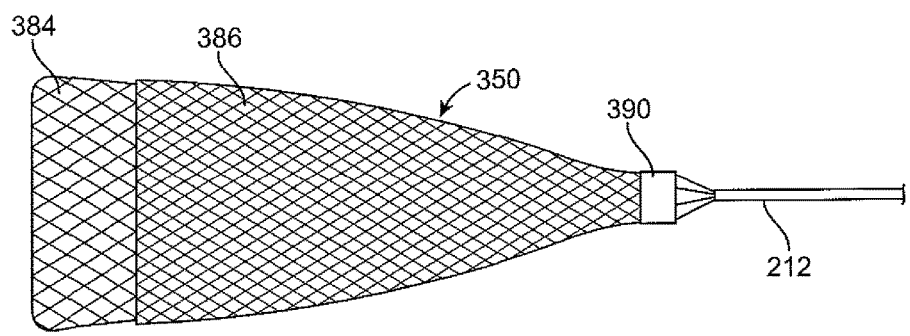
Figure 7C:
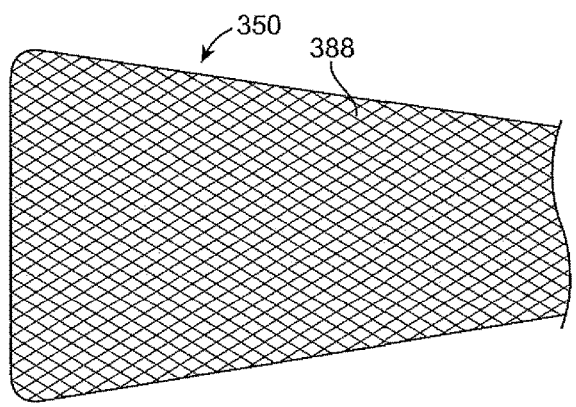

FIGS. 7A to 7C show addition variations of covers 350. FIG. 7A illustrates a cover in which the cover wall as defined by the inner layer 380 and outer layer 378 is set in a shape that varies along a length of the cover. For example, the end adjacent to the cover opening 382 can be set to a bulbous shape. Such a configuration assists in maintaining separation of layers 378 and 380, which aids in re-entry of the retrieval device. Additional configurations of cover walls that vary in thickness are within the scope of this disclosure.

One of the benefits of using a cover 350 as described herein is that the cover reduces flow through the vessel when deployed so that the retrieval device can remove the obstruction without the full force of the flow of blood opposing the obstruction. Typically, conventional devices relied upon the use of an inflated balloon to obstruct flow. However, use of a cover eliminates the need for total occlusion of blood flow. FIG. 7B illustrates a further improvement on a cover 350 that aids in flow reduction. As shown, the cover 350 includes a dense region 386 and a relatively less dense region 384. This configuration permits greater blood flow through the region 385 while region 386 reduces or prevents blood flow. Furthermore, the distal section of the cover is more flexible and conformable. Additional mesh layers can be added to any of the cover designs to alter flow characteristics or even provide reinforcement to the cover. Alternatively, or in combination, the braid density can be altered to adjust the porosity of the braid at different sections. Furthermore, additional braid layers can also be used to affect porosity of portions of the cover or even the entire cover. Deployment of a cover can reduce blood flow by 30% to 40%. Adding additional layers or coatings can additionally reduce flow.

FIG. 7C shows another variation of a cover 350 in which the mesh partially or totally is obscured using a polymeric coating 388 that reduces the permeability of the mesh design. Furthermore, drugs or other substances can be placed within the cover wall of any of the covers or can be deposited on the cover using the polymeric coatings. In some examples, the covers described herein can range from a length of 10 mm up to 50 mm. The OD at the opening of the cover can range from 7 mm and could range between 4 mm to 10 mm. Again, any range of dimensions is contemplated within the disclosure.

The covers described herein can further be stacked on a device. For example, two or more covers can be placed on a device to provide added protection.

The cover/re-entry devices described herein can be constructed of any material currently used in vascular applications, including those discussed above. Furthermore, fabrication of the cover from a DFT material can provide additional benefits as the entire cover remains radiopaque and can be imaged non-invasively. Furthermore, the covers can be provided with any type of medicament or bioactive substance either in a polymer that coats the mesh or in a delivery agent within the mesh or between layers. Such substances include tPA, urokinase, IIb/IIIa inhibitors, and other clot disruptors or inhibitors.

Figure 8:
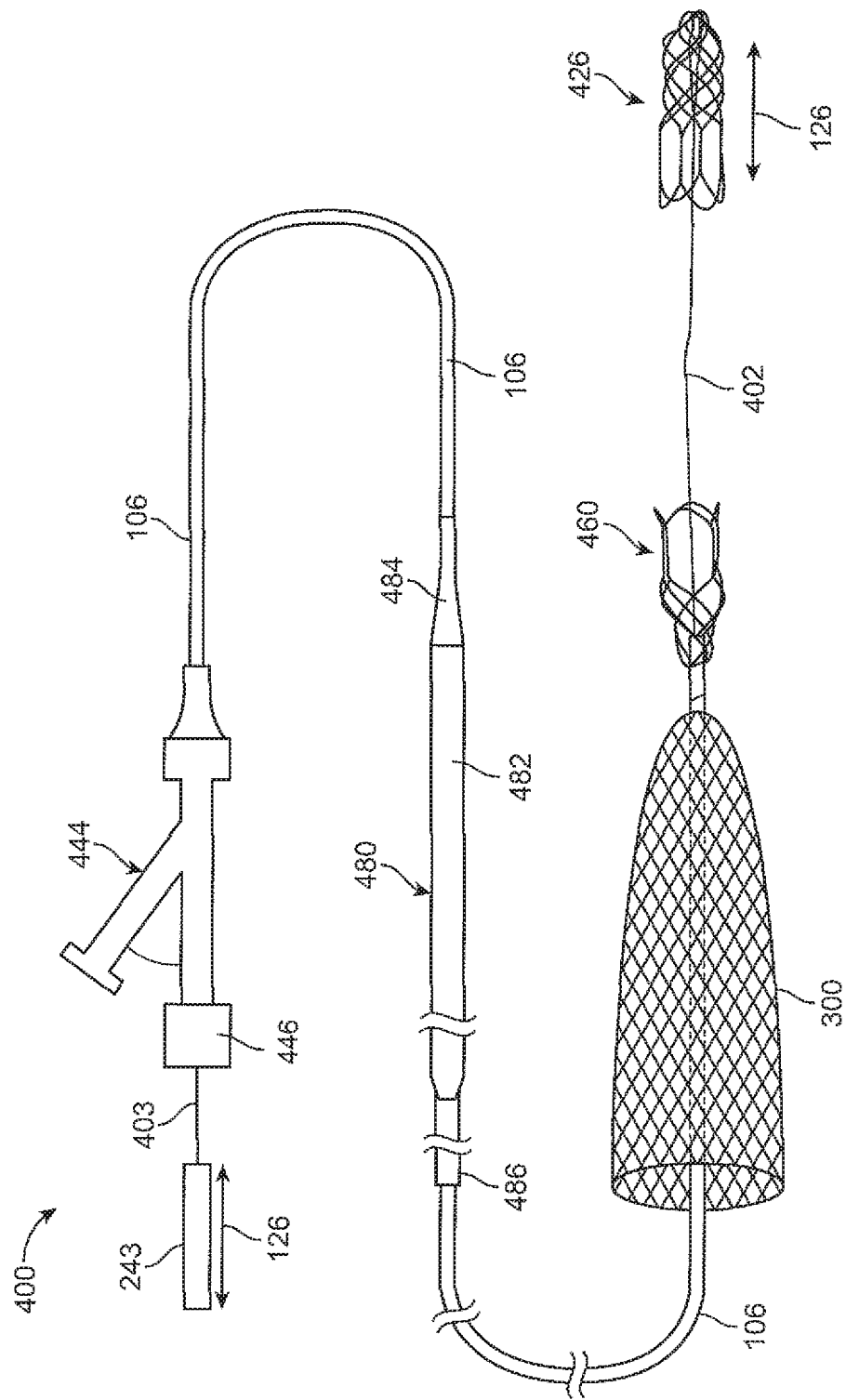
FIG. 8 illustrates a variation of a proximal and distal end of an additional retrieval device.

FIG. 8 illustrates another variation of a retrieval device 400 including a distal capture portion 426 coupled to one or more leading wires in the form of a main bundle 402. The main bundle extends through a sheath 106 that includes a proximal capture portion 460. The configuration of the retrieval device 400 can incorporate the proximal and distal capture portions discussed herein as well as various other configurations discussed in the commonly assigned patent applications noted above.

An end 464 of the proximal capture portion 460 is affixed to a distal end of the sheath 106. However, as noted above, other variations are within the scope of the disclosure. The main bundle 402 can optionally terminate at a handle 442. As noted above, in certain variations, the main bundle is joined to a stiffer wire or stiffer bundle of wires. This allows the device 400 to have a very flexible distal section with a relatively stiffer proximal section. The device 400 can have a proximal bundle 403 that comprises either the exposed wires or a covering/tube over the wires. In certain variations, the bundle or wire 402, 403 can be encapsulated with a coating. The device also includes a cover 300 adjacent to the retrieval device.

The proximal end of the sheath 106 includes a sheath handle 444. As discussed herein, axial movement of the bundle 402 or proximal bundle 403 (typically at the handle 442) results in movement 126, or translation of the bundle within the sheath 106. This action moves the distal capture portion 426 (as shown by arrows 126). In certain variations, the device 400 is loaded into a microcatheter (not shown but discussed above) that is delivered to the site of the obstruction and crosses the obstruction.

In some variations, the sheath hub 444 includes one or more locking hubs 446. Where actuation (either axial or rotational) of the locking hub 446 locks the main bundle 402 relative to the sheath handle 444 and sheath 106. It follows that such locking action also locks the distal capture portion 426 relative to the proximal capture portion 460. A variety of methods can be employed to increase a frictional interference between the locking hub 446 and the proximal bundle 403. As a result, when a physician determines a length of an obstruction, the physician can set a spacing between the capturing portions 426 460 by locking the proximal bundle 403 relative to the sheath hub 444. Accordingly, the proximal bundle 403 can include any type of incremental markings to allow the physician to readily determine a spacing of the capturing portions. As illustrated, the sheath hub 444 can include additional injection ports to deliver fluid or other substances through the sheath 106.

As noted above, the device 400 can be used with a micro-catheter. In those variations it is important that the device 400 is loaded without damaging the distal bundle 402, capture portions 426 460, and/or sheath 106. As a result, the device 400 can include an optional cover 486 that reduces the proximal capture portion 460 (and or the distal capture portion 426) for loading within the microcatheter and/or sheath 106.

Another variation of the device 400 includes an insertion tool 480 slidably affixed to the sheath 480. Because variations of the device 400 can be extremely flexible, the insertion tool 480 can be used to provide column strength to the sheath 106, bundle 402 or other components as the device 400 is pushed into the microcatheter. The insertion tool comprises a rigid section 482 and a frictional coupler 484. The rigid section 282 has a column strength that supports the device 400 to prevent buckling. The frictional coupler 484 can be a flexible material that allows an operator to squeeze or grip the coupler 484 to create a temporary frictional interface between the loading tool 480 and the device 400 (typically the sheath 106). Such an action allows axial advancement of the device 400 as the loading tool 480 is advanced into the microcatheter. Once the rigid section 482 is fully inserted into the microcatheter, the operator releases the frictional coupler 484 and can withdraw the loading tool 480 from the catheter without withdrawing the device 400. The insertion tool 480 can also include an optional loading tube 486 slidably coupled to the rigid section 482. When used, the cover 486 can withdraw the proximal and distal capturing portion 226 and 260 within the loading tube 486. The loading tube 486 then couples to a microcatheter allowing the capturing portions to advance therein as the rigid section 482 and frictional coupler 484 advance the device 400 relative to the loading tube 486.

Figure 9A:
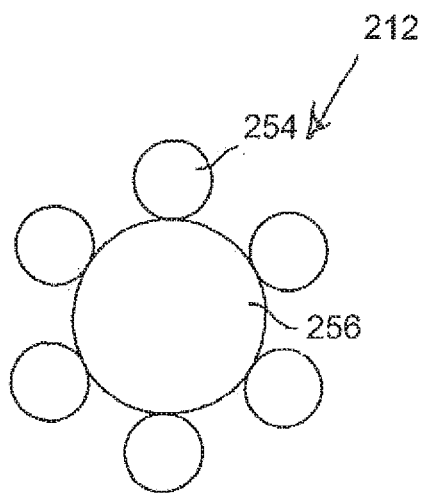
FIGS. 9A to 9C illustrate wires of different constructions within a delivery wire or shaft.
Figure 9B:
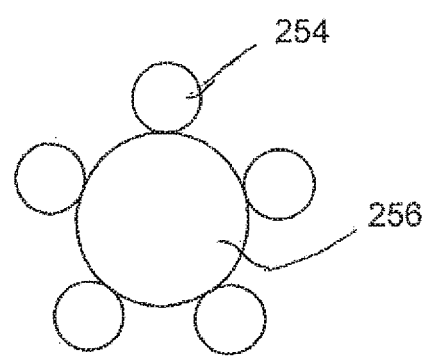
Figure 9C:
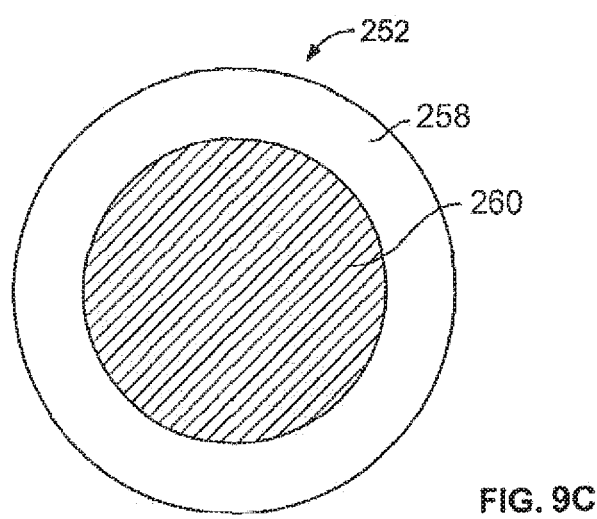

FIGS. 9A to 9C show cross sectional views taken along the line 9A-9A in FIG. 2A. As shown, the wire form construction described herein allows for a number of configurations depending on the particular application. For example, the individual wires 254 (as discussed herein) may themselves comprise a bundle of smaller wires or filaments. In addition, the wires can be selected from materials such as stainless steel, titanium, platinum, gold, iridium, tantalum, Nitinol, alloys, and/or polymeric strands. In addition, the wires used in a device may comprise a heterogeneous structure by using combinations of wires of different materials to produce a device having the particular desired properties. For example, one or more wires in the device may comprise a shape memory or superelastic alloy to impart predetermined shapes or resiliency to the device. In some variations, the mechanical properties of select wires can be altered. In such a case, the select wires can be treated to alter properties including: brittleness, ductility, elasticity, hardness, malleability, plasticity, strength, and toughness.

The device may include a number of radiopaque wires, such as gold and platinum for improved visibility under fluoroscopic imaging. In other words, any combination of materials may be incorporated into the device. In addition to the materials, the size of the wires may vary as needed. For example, the diameters of the wires may be the same or may vary as needed.

In addition, the individual wires may have cross-sectional shapes ranging from circular, oval, d-shaped, rectangular shape, etc. FIG. 9A illustrates one possible variation in which a number of circular wires 254 are included around another larger wire 256. Moreover, the device is not limited to having wires having the same cross-sectional shape or size. Instead, the device can have wires having different cross-sectional shapes. For example, as shown in FIG. 9B, one or more wires 256 can have a different cross-sectional shape or size than a reminder of the wires 254. Clearly, any number of variations is within the scope of this disclosure. This construction can apply to the retrieval portion, capturing portion and/or the covering portion of the device.

To illustrate one such example, a device can have 8-12 wires made of 0.003" round superelastic material (e.g., Nitinol). The device may additionally have 2-4 wires made from 0.002" platinum for fluoroscopy. Of the 8-12 Nitinol wires, 1-4 of these wires can be made of a larger diameter or different cross-section to increase the overall strength of the device. Finally, a couple of polymer fibers can be added where the fibers have a desired surface property for clot adherence, etc. Such a combination of wires provides a composite device with properties not conventionally possible in view of other formation means (such as laser cutting or etching the shape from a tube or joining materials with welds, etc.). It will be appreciated that any number of permutations is possible given the principles of the invention.

In another example, the device may be fabricated from wires formed from a polymeric material or composite blend of polymeric materials. The polymeric composite can be selected such that it is very floppy until it is exposed to either the body fluids and or some other delivered activator that causes the polymer to further polymerize or stiffen for strength. Various coatings could protect the polymer from further polymerizing before the device is properly placed. The coatings could provide a specific duration for placement (e.g., 5 minutes) after which the covering degrades or is activated with an agent (that doesn't affect the surrounding tissues) allowing the device to increase in stiffness so that it doesn't stretch as the thrombus is pulled out. For example, shape memory polymers would allow the device to increase in stiffness.

In another variation, one or more of the wires used in the device may comprise a Drawn Filled Tube (DFT) such as those provided by Fort Wayne Metals, Fort Wayne, Ind. As shown in FIG. 9C, such a DFT wire 252 comprises a first material or shell 258 over a second material 260 having properties different from the outer shell. While a variety of materials can be used, one variation under the present devices includes a DFT wire having a superelastic (e.g., Nitinol) outer tube with a radiopaque material within the super-elastic outer shell. For example, the radiopaque material can include any commercially used radiopaque material, including but not limited to platinum, iridium, gold, tantalum, or similar alloy. One benefit of making a capturing portion from the DFT wire noted above, is that rather than having one or more markers over the capturing portion, the entire capturing portion can be fabricated from a super-elastic material while, at the same time, the super-elastic capturing portion is made radiopaque given the core of radiopaque material within the super-elastic shell. Clearly, any composite DFT wire 252 can be incorporated into the system and capturing portions described herein.

Another aspect applicable to all variations of the devices is to configure the devices or portions thereof that engage the obstruction to improve adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction. Coatings may also be combined with the capturing portions or catheter to improve the ability of the device to encapsulate and remove the obstruction (e.g., a hydrophilic coating).

Such improvements may also be mechanical or structural. Any portion of the capturing portion can have hooks, fibers, or barbs that grip into the obstruction as the device surrounds the obstruction. The hooks, fibers, or barbs 370 can be incorporated into any portion of the device. However, it will be important that such features do not hinder the ability of the practitioner to remove the device from the body.

In addition to additives, the device can be coupled to an RF or other power source (such as 14 or 16 in FIG. 1), to allow current, ultrasound or RF energy to transmit through the device and induce clotting or cause additional coagulation of a clot or other the obstruction.

Figure 10A:
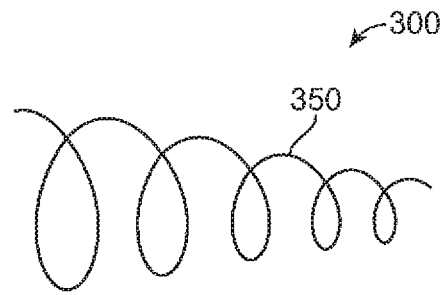
FIGS. 10A to 10E illustrate additional variations of covers for use as described above.
Figure 10B:
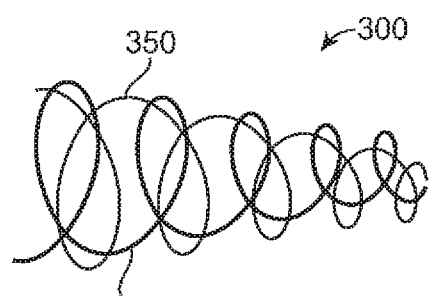
Figure 10C:
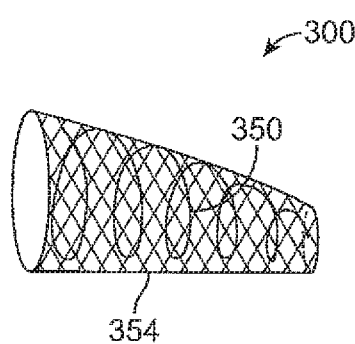
Figure 10D:
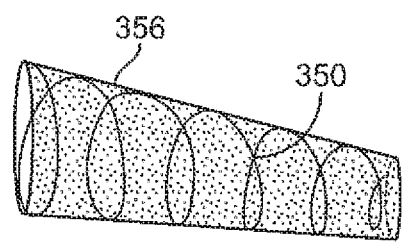
Figure 10E:
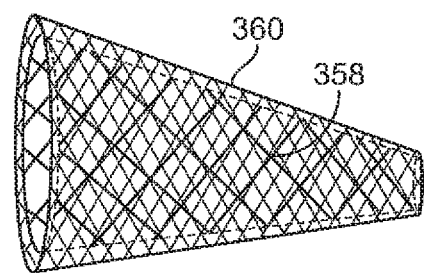

FIGS. 10A to 10E illustrate additional variations of covers 300 for use as described above. For example, as show in FIG. 10A, a cover 300 can comprise a single wire, coil, or laser cut tube 350. Alternatively, as shown in FIG. 10B, the cover 300 can comprises two or more 350, 352 wires or coils. FIG. 10C shows a cover 300 comprising a coil 350 inside a mesh structure 354. A variation of the device shown in FIG. 10C can include a compliant atraumatic mesh 354 that is radially supported by the coil (whether interior or exterior to the mesh). The coil 350 provides the outward force against the vessel. FIG. 10D illustrates a polymeric film or membrane 356 coupled to a coil 350. The polymeric film 356 can be permeable to fluid flow or impermeable. FIG. 10E illustrates a dual layer braid construction having an inner braid 358 and an outer braid 360. The braids can be constructed to have unique properties. For example, the inner braid 358 can be composed of fewer wires or larger diameter wires, such that it provides an expansion force against the vessel wall. The outer braid 360 can comprise a softer construction and increased compliance. Accordingly, it can be comprised of a number of smaller diameter wires having a denser pattern to provide increased surface area to protect the obstruction as it is removed from the body. Alternatively, these two constructional elements (e.g., braids of varying diameters) can be combined into a single layer or even multiple layers for the cover.

Figure 11A:
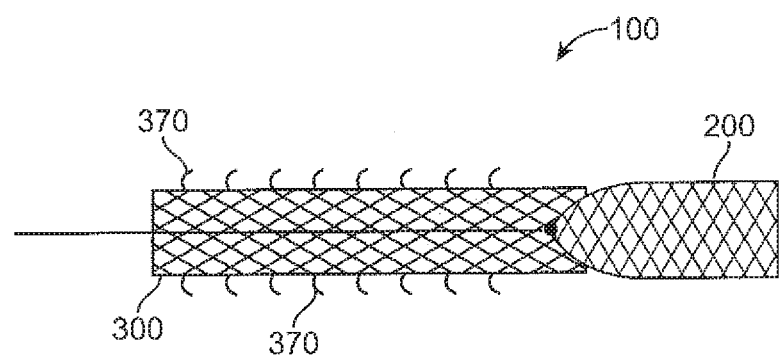
FIGS. 11A to 11C illustrate additional variations of covers for use with the devices and methods described herein.

FIG. 11A illustrates yet another variation of a device 100 having a retrieval structure 200 and cover 300 where the cover is simply fabricated from the same material as the retrieval structure so long as it functions as described herein. The variation can optionally include one or more barbs 370 to increase resistance against a vessel wall.

Figure 11B:
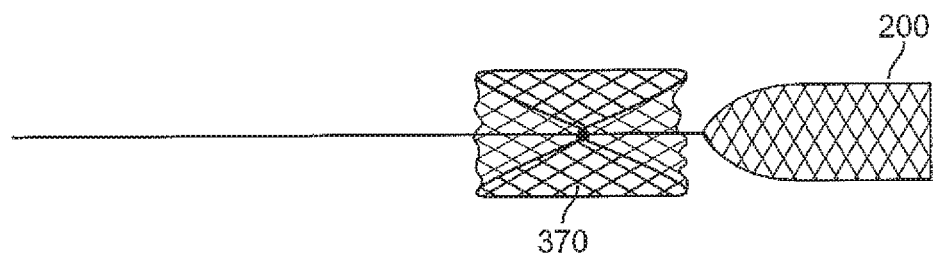
Figure 11C:
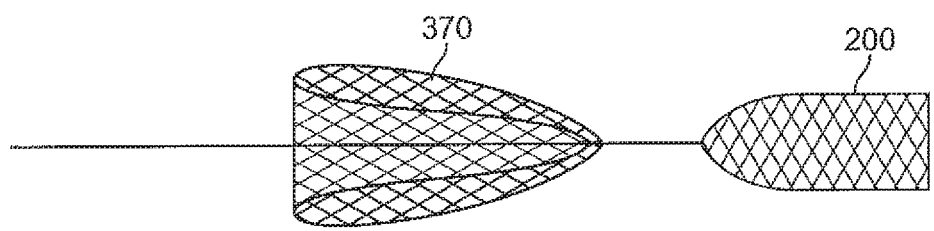

FIGS. 11B and 11C illustrate a variation where the cover 300 comprises a balloon material. FIG. 11B illustrates the balloon cover 370 prior to deployment. FIG. 11C illustrates the balloon cover 370 once deployed.

Figure 12A:
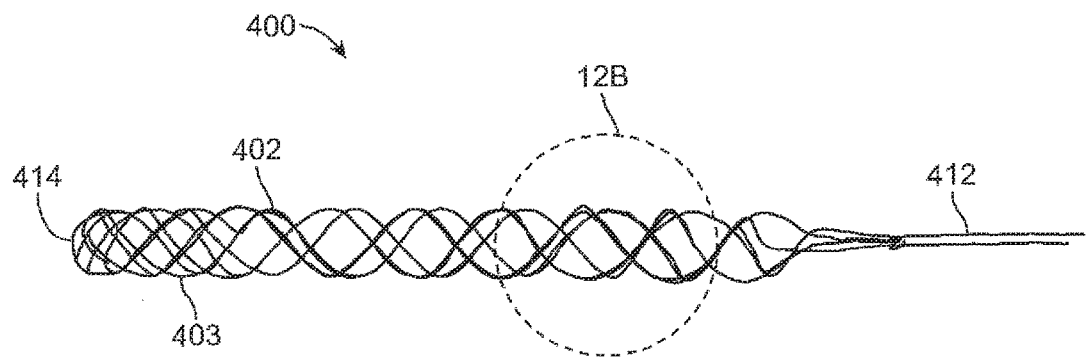
FIGS. 12A to 12F illustrate various stent designs for increasing the ability of a stent to adhere to an occlusion within a vessel.

The retrieval devices described herein can optionally comprise elongated stents 400 as shown in FIGS. 12A to 12E. These stents 400 can include any number of features to better assist the stent 400 in becoming enmeshed into the obstruction. For example, FIG. 12A illustrates a variation of a stent 400 affixed to a shaft 412. As noted herein, the shaft 412 can include a lumen extending therethrough. Alternatively, the shaft 412 can include a solid member with the stent 400 affixed to a distal end thereof. The variation shown in FIG. 12A includes a stent where a distal end 414 that is "closed off" by intersecting elements or wires 402 403. Accordingly, any of the variations of the stents disclosed herein can include an open lumen type stent or a closed lumen type stent as shown in FIG. 12A. As noted herein, the wires forming the stent 400 can comprise a single wire that is wound from a first direction (e.g., from proximal to distal) and then wound back in a second direction (e.g., from distal to proximal).

Figure 12B:
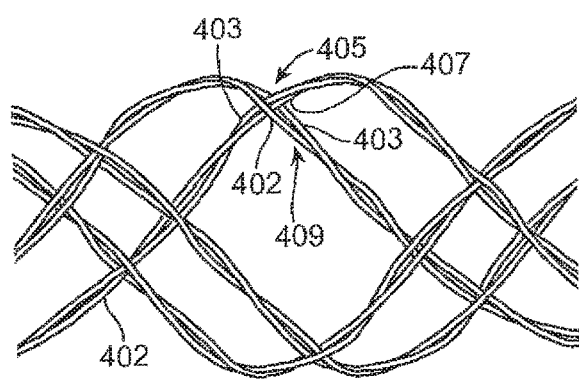

FIG. 12A also illustrates a stent 400 comprised of twisted wires 402 or elements. For example, FIG. 12B shows a magnified view of the section 12B in FIG. 12A. As illustrated, the elements 402 and 403 are twisted to increase the surface area at the exterior perimeter of the stent 400. The twisting or spiraling of the elements 402 403 creates additional surface area to increase the ability of the stent 400 to capture debris, thrombus, foreign body, etc. as the stent is expanded against the debris. The twisting elements 402 403 can twist along the entire length of the stent 400 or along one or more portions of the stent. In certain variations, the twisting of the elements 402 403 is sufficiently loose such that as the stent expands into a clot or obstruction, the twisted pairs slightly separate to allow material to become trapped between the elements making up the pairs. The construction shown in FIGS. 12A and 12B also provide an additional benefit to a retrieval stent. In the illustrated variation, the twisted or spiraling elements interlock with crossing elements to form intersections 405 that provided added radial expansive force. As shown, a first twisted element 407 passes in between elements 402 403 of an intersecting element 409. When in an expanded state, the element on the interior of the intersection 405 (in this case element 403) provides an added outward radial force against the intersection 405. However, since the elements are not affixed but instead are slidable at the intersection 405, the force required to linearlize and compress the stent 400 is reduced due to the fact that the intersections are not affixed but slidable over the adjacent elements. This reduced linearization force allows the stent to be compressed to a small diameter for positioning within a microcatheter but allow for a significant radial expansive force once removed from the microcatheter. This design allows for a reduction in radial force of the stent against the vessel wall when the stent is pulled and removed from the vessel. However, this design also provides a high degree of radial force due to the interweaving of elements when the stent is deployed in the vessel prior to withdrawal of the stent.

Figure 12C:
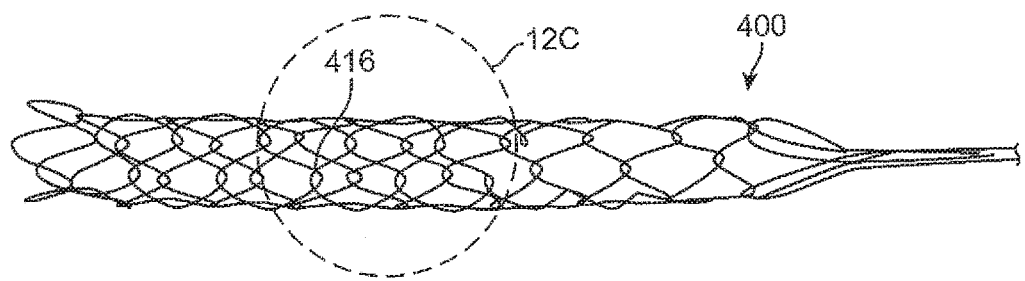
Figure 12D:
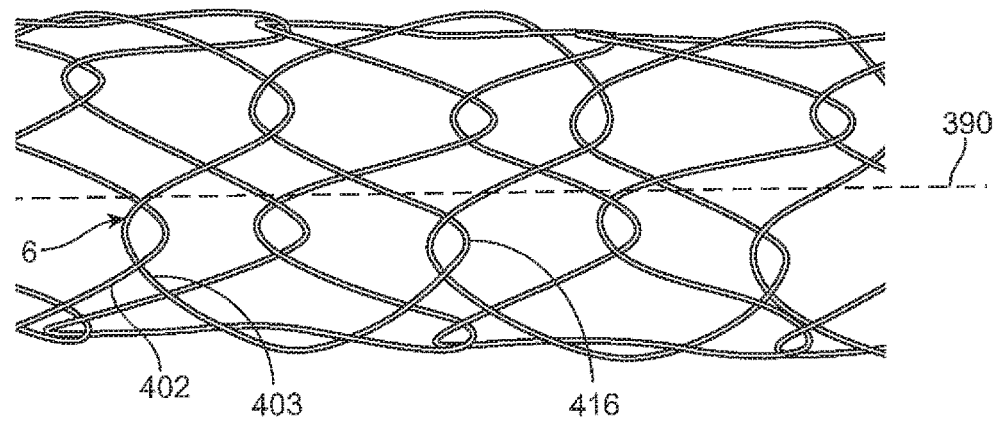
Figure 12E:
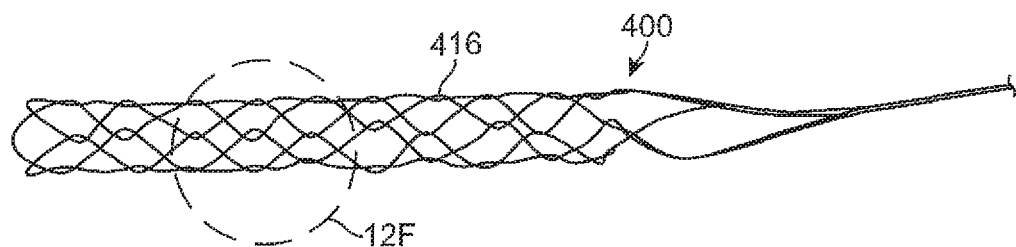
Figure 12F:
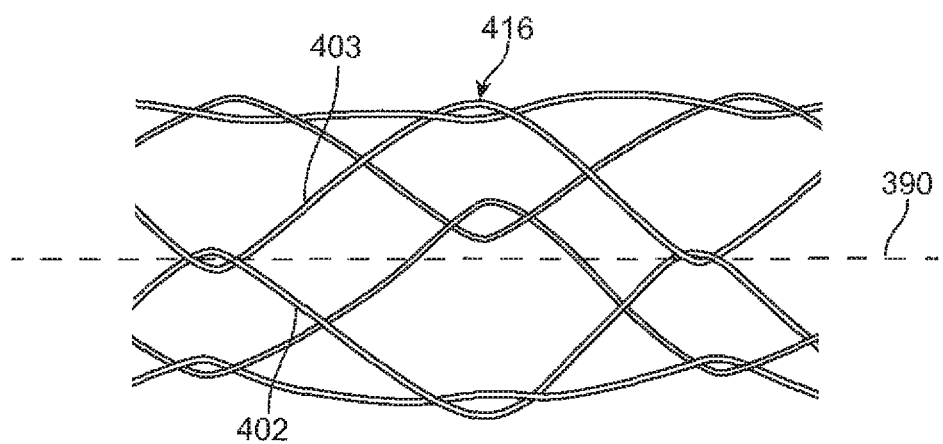

FIGS. 12C to 12F illustrate another variation of types of stents 400 that have an irregular surface at an exterior of the stent 400 that is formed by an intersection of elements 402 and 403. The intersection or crossing of the elements forms a type of barb or knuckle 416 that creates an irregular surface on the exterior of the stent 400. FIG. 12C illustrates a variation of a stent 400 having a plurality of knuckles 52 that are radially spaced about an axis 390 of the stent 400. FIG. 12E shows another variation of a stent 400 with knuckles 416 aligned with an axis 390 of the stent 400 as shown in FIG. 12D. Although the figures show the axial and radial aligned knuckles 416 on separate devices, both types of knuckles 416 can be incorporated into a single stent structure. Varying the alignment of knuckles can permit increased radial force as the stent expands into the obstruction or increased flexibility as the stent navigates through tortuous anatomy.

Figure 12G:
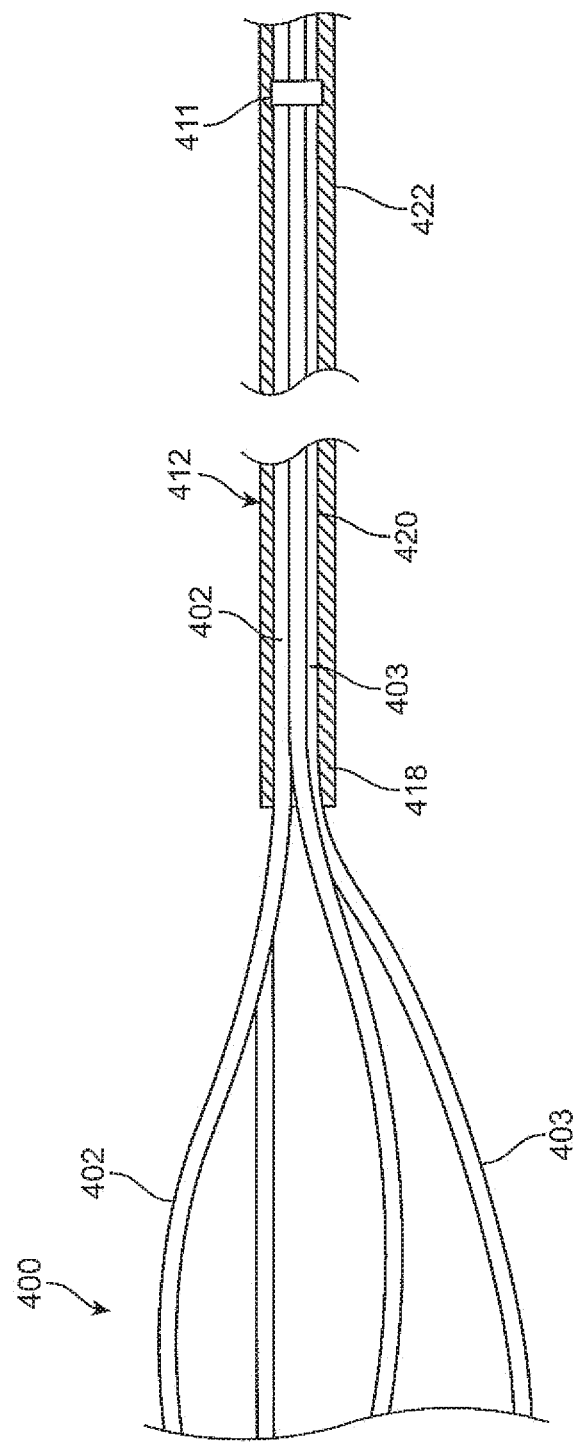
FIG. 12G illustrates a proximal end of the stent structure.

FIG. 12G illustrates a proximal end of the stent structure 400 as shown, a plurality of elements 402 and 403 extend along the shaft 412 and diverge to form the fluid permeable closed proximal end of the stent structure 400. The elements 402 and 403 that extend along the shaft 412 can be covered by a sheath, tube, spiral cut tube, or any structure 418 that prevents separation of the elements 402 403. A variation of the stent structure 402 includes a construction where the elements 402 and 403 are not glued, welded, or have any similar type of joint in the distal portion 420 of the shaft 412. Instead, the joint 411 is located proximal to the distal section of the shaft 412 in an intermediate section 422. Because joints or other similar features reduce flexibility of the joined structure, positioning the joints 411 in a proximal area allows the distal portion 420 of the shaft to remain flexible.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, a mild formalin, or aldehyde solution.

Figure 13A:
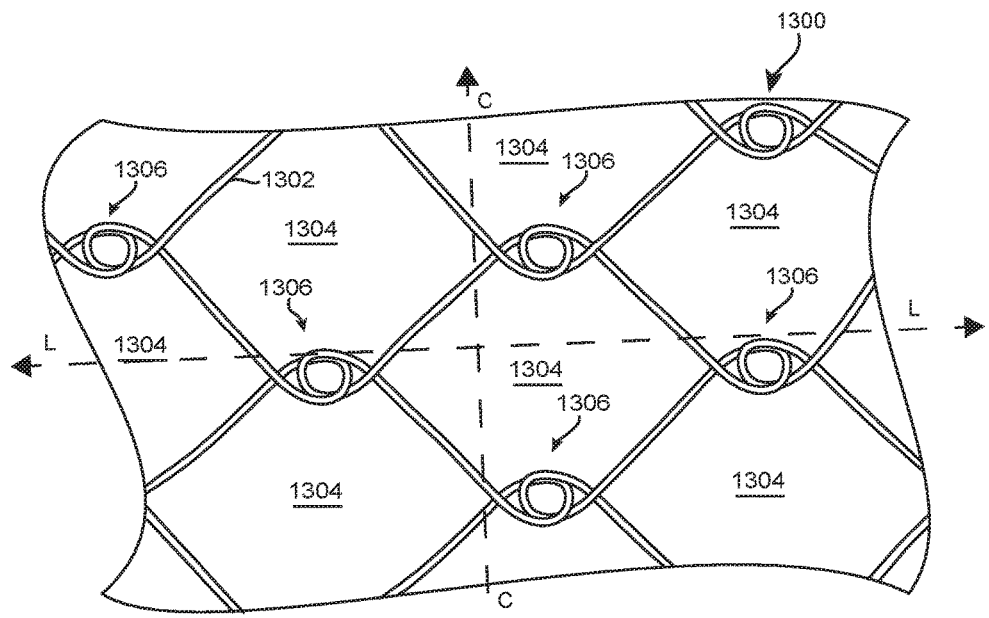
FIG. 13A shows a portion of an expandable structure in accordance with an embodiment of the present technology.
Figure 15:
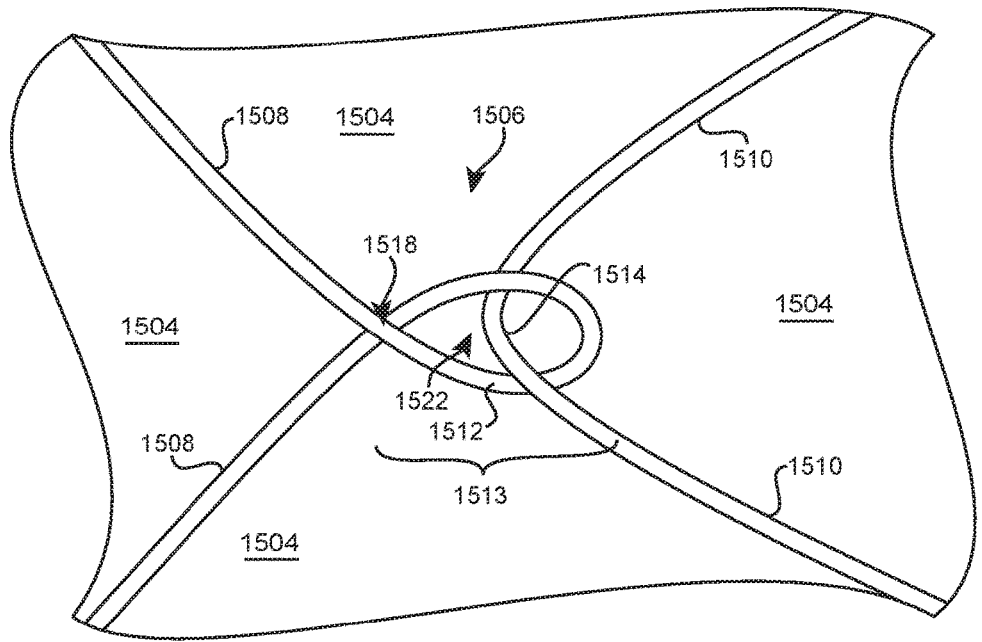
FIGS. 15-17 show enlarged views of different joints in accordance with several embodiments of the present technology.
Figure 16:
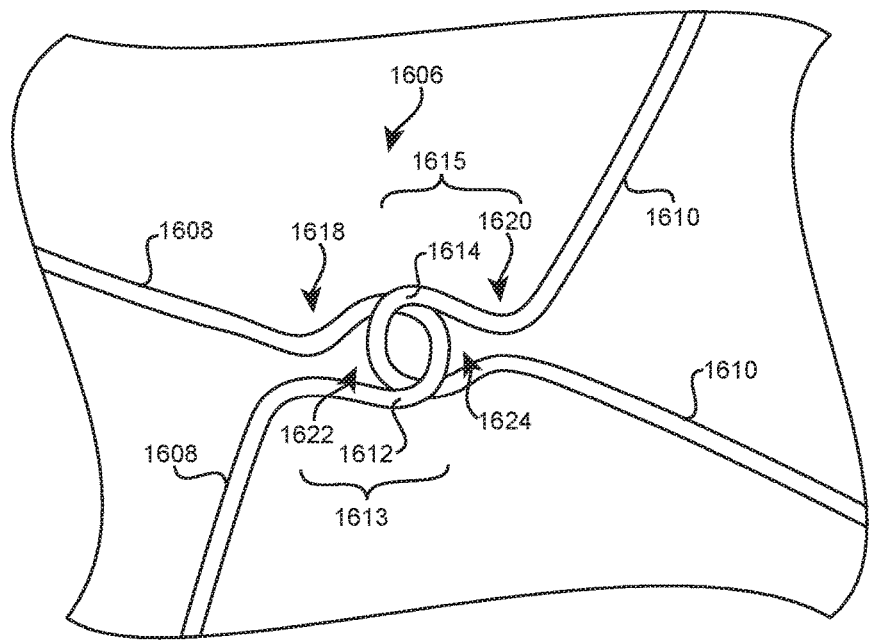
Figure 17:
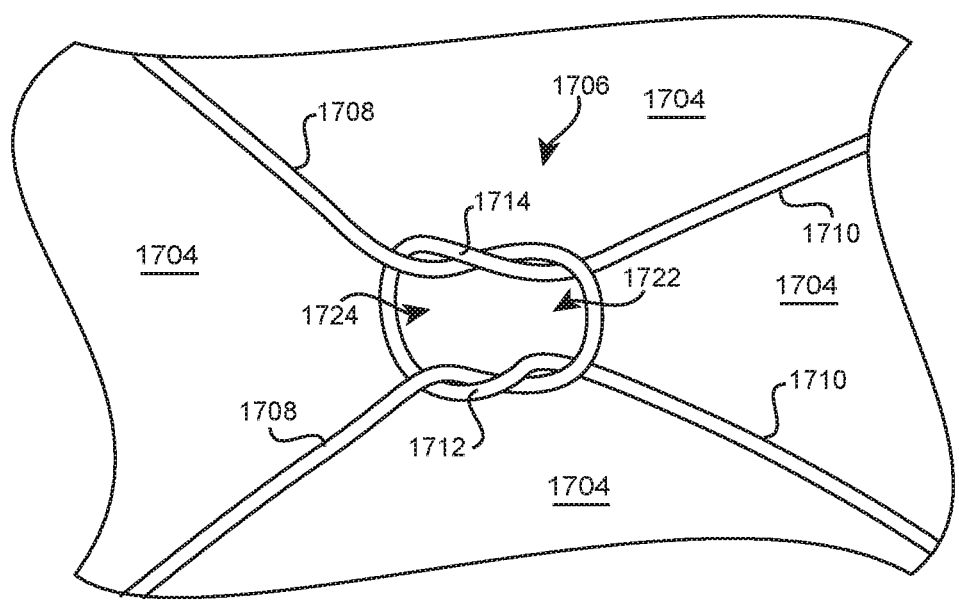

FIG. 13A is a side view of a portion of an expandable structure 1300 configured to be positioned in a blood vessel. In particular, FIG. 13A depicts a configuration of strands 1302, cells 1304 and joints 1306 in a sidewall of the expandable structure 1300, which can comprise an expandable, generally tubular vascular device such as a stent (e.g. an aneurysm bridging stent), a flow diverter, or a thrombectomy device (e.g. a stent retriever comprising the expandable structure 1300 in tubular form and a shaft or push member attached to and extending proximally from a proximal end of the expandable structure 1300). FIGS. 15-17 depict additional or alternative configurations of strands, cells and joints that can be employed in the expandable structure 1300 and the various medical or vascular devices that may incorporate the expandable structure 1300. The expandable structure 1300 can, in some embodiments, be similar to the stent 400, except as further described herein.

The expandable structure 1300 is formed of one or more interwoven elongate strands 1302, such as metal wires or polymer filaments, that are arranged to form a plurality of cells 1304 and connected at a plurality of joints 1306. As shown in the enlarged view of one of the joints 1306 in FIG. 13B, at least one of the joints 1306 of the expandable structure 1300 comprises a first strand 1308 and a second strand 1310 having first and second interlocking portions 1312 and 1314, respectively. The first strand 1308 and the second strand 1310 may be two separate strands, or they may be different portions of a single, continuous strand (e.g., a single, continuous filament). As described in greater detail below, the first and second interlocking portions 1312, 1314 may move relative to one another at the joint 1306 to allow the expandable structure 1300 to longitudinally shorten for conforming to the inside or near side of a tight bend in the vasculature. The first and second interlocking portions 1312, 1314 also form first and second restrictions 1318 and 1320, respectively, that limit longitudinally compressive disengagement of the first and the second strand 1308 and 1310 at the joint 1306, provide column strength to enhance pushability, and prevent longitudinal shortening of the expandable structure 1300 beyond a predetermined length.

Figure 13B:
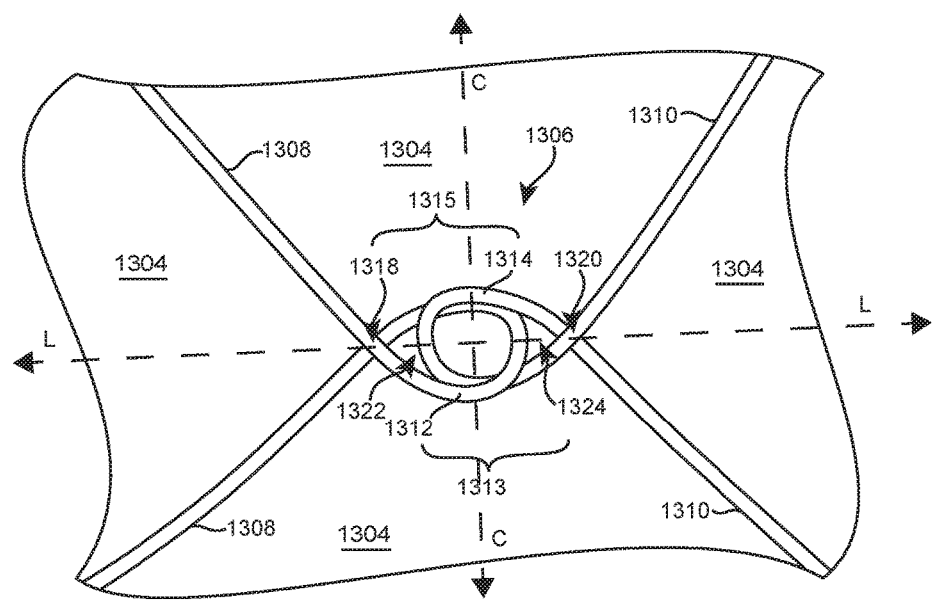
FIG. 13B is an enlarged view of one of the joints of the expandable structure shown in FIG. 13A in accordance with an embodiment of the present technology.

As shown in FIG. 13B, along the first interlocking portion 1312, the first strand 1308 extends in a first direction towards the joint 1306, then bends back on itself, and then extends in a second direction away from the joint 1306 such that the first strand 1308 crosses over itself. The intersection of the first strand 1308 with itself forms the first restriction 1318 that limits movement of the second interlocking portion 1314 relative to the first interlocking portion 1312. The bent portion 1313 of the first strand 1308 (i.e., the length of the first strand 1308 between the intersecting portions of the first strand 1308) and the first restriction 1318 together enclose an opening 1322 in the first interlocking portion 1312. Although the bent portion 1313 of the first strand 1308 is shown in FIG. 13B as having a looped or curved shape, in other embodiments the bent portion 1313 may have any shape or configuration so long as the first strand 1308 changes direction along the bent portion 1313. For example, in some embodiments one or more regions of the bent portion 1313 may be generally linear.

Along the second interlocking portion 1314, the second strand 1310 extends in a first direction toward the joint 1306, then bends back on itself, and then extends in a second direction away from the joint 1306 such that the second strand 1310 crosses over itself. The intersection of the second strand 1310 with itself forms the second restriction 1320 that limits movement of the second interlocking portion 1314 relative to the first interlocking portion 1312. The bent portion 1315 of the second strand 1310 (i.e., the length of the second strand 1310 between the intersecting portions of the second strand 1310) and the second restriction 1320 together enclose an opening 1324 in the second interlocking portion 1314. Although the bent portion 1315 of the second strand 1310 is shown in FIG. 13B as having a looped or curved shape, in other embodiments the bent portion 1315 may have any shape or configuration so long as the second strand 1310 changes direction along the bent portion. For example, in some embodiments one or more regions of the bent portion 1315 may be generally linear.

As shown in FIG. 13B, the bent portion 1315 of the second strand 1310 extends through the opening 1322 in the first strand 1308 (or vice versa, i.e., the bent portion 1313 of the first strand 1308 extends through the opening 1324 in the second strand 1310). As such, the bent portion 1313 of the first strand 1308 and the bent portion 1315 of the second strand 1310 are interlocked and prevented from disengaging one another as the structure 1300 is longitudinally compressed by the first and second restrictions 1318 and 1320.

In the embodiment shown in FIGS. 13A and 13B, all of the joints are configured as joint 1306. In other embodiments, some of the joints of the expandable structure 1300 can be other types of joints. For example, in some embodiments, the expandable structure 1300 can include a plurality of joints 1306 and a plurality of cross-over joints (i.e., where one strand crosses over the other strand and the two strands are allowed to move relative to one another). In other embodiments, any of the joints disclosed herein (e.g., joint 1306, joint 1506, joint 1606, joint 1706, barb or knuckle 416, etc.) can be combined in a single expandable structure. Moreover, the expandable structure 1300 can have any of the joints and/or proximal and/or distal regions as are detailed with respect to FIGS. 1-12G.

The strand(s) 1302 of any of the expandable structures herein (including expandable structure 1300) may be formed from one or more materials, including stainless steel, nickel-titanium alloy (nitinol), tantalum, elgiloy, various polymer materials, such as poly(ethylene terephthalate) (PET) or polytetrafluoroethylene (PTFE), or bioresorbable materials, including bioresorbable polymers such as levorotatory poly-lactic acid (L-PLA) or polyglycolic acid (PGA). In some embodiments the material comprises a superelastic material, such as nitinol metal, that will withstand tight compression in a delivery state and self-expand to a deployed state at the treatment site. Alternatively, the expandable structure 1300 of the present invention may be constructed from a material (e.g., stainless steel) that can be mechanically enlarged once positioned in the blood vessel, such as through balloon expansion.

Although the joints 1306 are shown generally aligned in a longitudinal direction (as demonstrated by line L), in other embodiments, one or more of the joints 1306 may be aligned in a circumferential direction (as demonstrated by line C).

FIGS. 14A-14D illustrate the expandable structure 1300 and a method for positioning the expandable structure 1300 around a tight bend within a blood vessel. As used herein, "tight bend" is used to refer to a portion of a blood vessel with a bend angle of at least 90 degrees, or in some instances, at least 135 degrees.

Figure 14A:
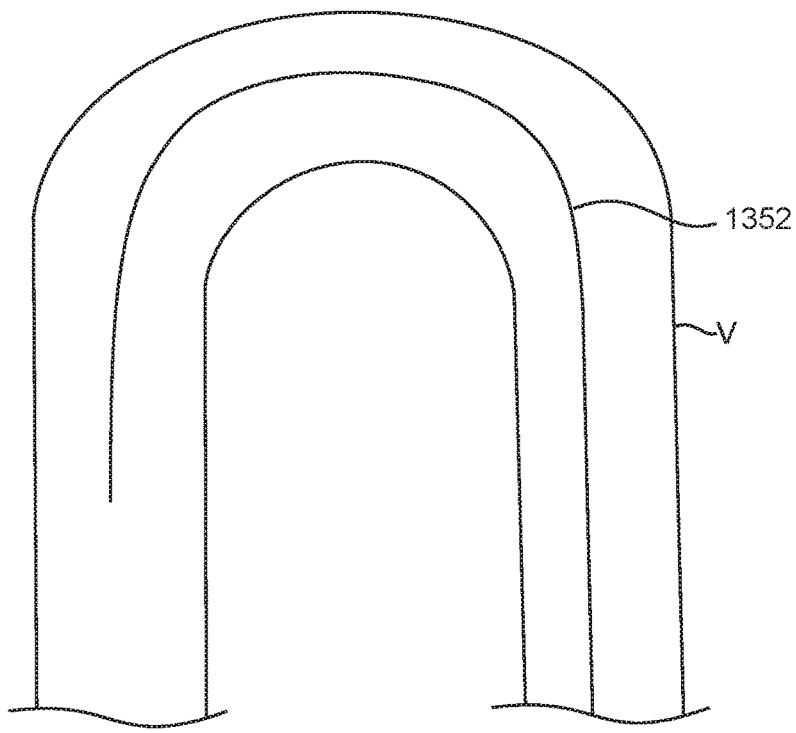
FIGS. 14A-14D illustrate a method of positioning an expandable structure around a tight bend in a blood vessel in accordance with the present technology.

As shown in FIG. 14A, a guidewire 1352 may first be advanced intravascularly to the treatment site from an access site, such as a femoral or a radial artery. A guide catheter or microcatheter 1354 may then be advanced along the guidewire 1352 until at least a distal portion of the guide catheter 1354 is positioned at the treatment site. In these and other embodiments, a rapid-exchange technique may be utilized. Image guidance, e.g., computed tomography (CT), fluoroscopy, angiography, intravascular ultrasound (IVUS), optical coherence tomography (OCT), or another suitable guidance modality, or combinations thereof, may be used to aid the clinician's positioning and manipulation of the expandable structure 1300. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the expandable structure 1300. Further, in some embodiments, image guidance components (e.g., IVUS, OCT) may be integrated with the delivery catheter and/or run in parallel with the delivery catheter to provide image guidance during positioning of the expandable structure 1300.

Figure 14B:
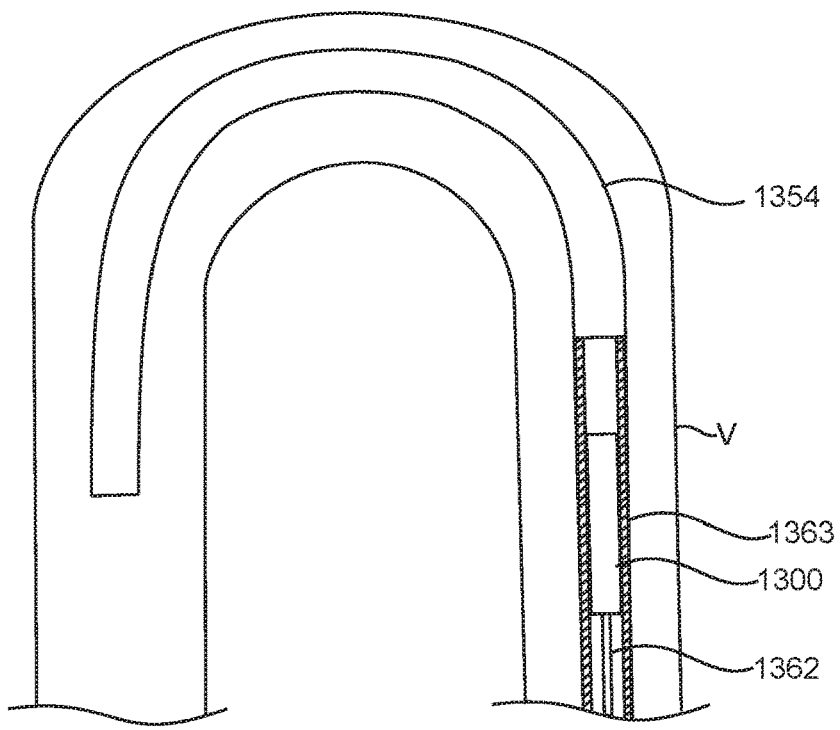
Figure 14C:
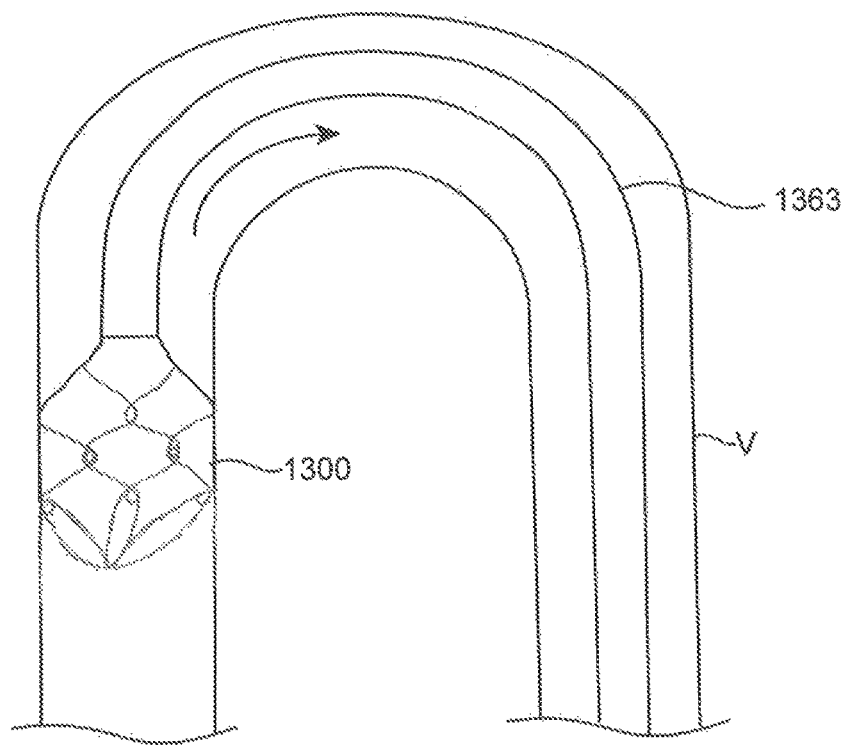

Once the guide catheter or microcatheter 1354 is positioned at the treatment site, the guidewire 1352 may be withdrawn. As shown in FIG. 14B, a delivery assembly 1360 carrying the expandable structure 1300 may then be advanced distally through the guide catheter 1354 to the treatment site, and the guide catheter 1354 may be withdrawn. In some embodiments, the delivery assembly 1360 includes an elongated shaft 1362 which is permanently or detachably coupled to a proximal region of the expandable structure 1300, and an optional delivery sheath 1363 surrounding the expandable structure 1300 to constrain the expandable structure 1300 in a low-profile configuration for delivery to the treatment site. As shown in FIG. 14C, the elongated shaft 1362 may be advanced to push the expandable structure 1300 distally from a distal end of the delivery sheath 1363 or guide catheter/microcatheter 1354. As the expandable structure 1300 exits the delivery sheath, the expandable structure 1300 expands radially outwardly into contact with the vessel wall, and/or into contact with or into an interlocking or gripping relationship with any adjacent thrombus (or other obstructions such as plaque). Where present, the delivery sheath 1363 may be withdrawn to release the expandable structure 1300.

Figure 14D:
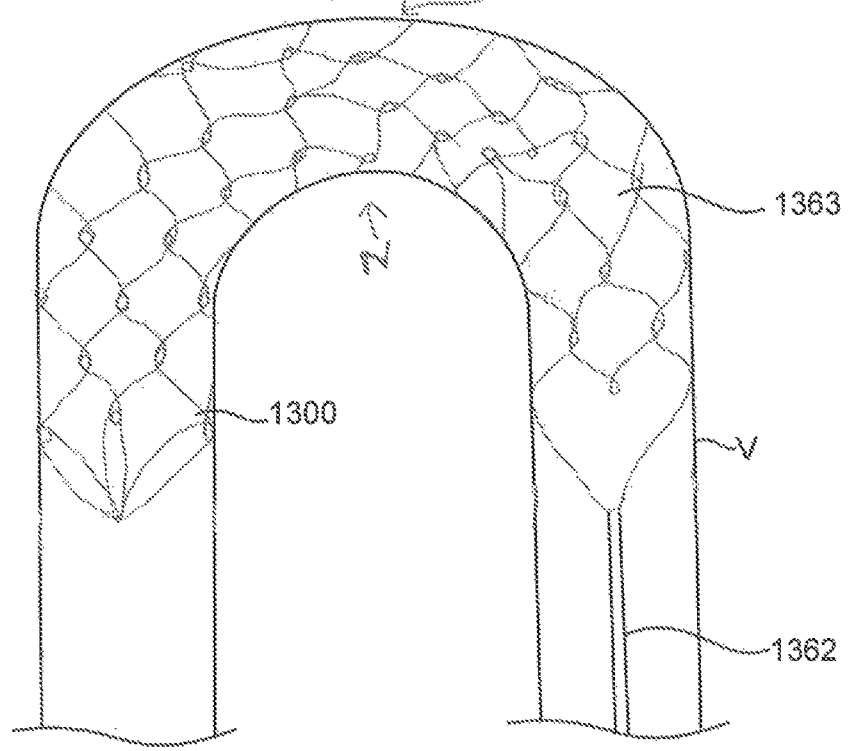

As best shown in FIGS. 14C and 14D, the expandable structure 1300 expands to conform to the vessel wall around the tight bend in the vasculature. Unlike conventional braided or laser-cut stents, the expandable structure 1300 maintains apposition with the vessel wall along the portion of the vessel wall comprising the bend. For example, along portions of the expandable structure 1300 experiencing tensile forces (e.g., at the far side F of the bend), the first and second interlocking portions 1312 and 1314 move longitudinally away from one another such that a distance between the first and second restrictions 1318 and 1320 increases (relative to a relaxed state). Along portions of the expandable structure 1300 experiencing compressive forces (e.g., at the near side N of the bend, or circumferentially opposite the portions under tensile stress), the first and second interlocking portions 1312 and 1314 move longitudinally toward one another such that a distance between the first and second restrictions 1318 and 1320 decreases (relative to a relaxed state).

FIGS. 15-17 show several embodiments of different joints for use in the expandable structures and/or retrieval structures of the present technology. FIG. 15, for example, shows an enlarged view of a joint 1506 comprising a first strand 1508 and a second strand 1510 having first and second interlocking portions 1512 and 1514, respectively. The first strand 1508 and the second strand 1510 may be two separate strands, or they may be different portions of a single, continuous strand (e.g., a single, continuous filament). As described in greater detail below, the first and second interlocking portions 1512 and 1514 may move relative to one another at the joint 1506 to allow the expandable structure 1500 to longitudinally compress for conforming to tight bends in the vasculature. The first interlocking portion 1512 also forms a restriction 1518 that limits longitudinally compressive disengagement of and longitudinal displacement between the first and the second strand 1508 and 1510 at the joint 1506, provides column strength to enhance pushability, and prevents longitudinal shortening of the expandable structure beyond a predetermined length.

As shown in FIG. 15, along the first interlocking portion 1512, the first strand 1508 extends in a first direction towards the joint 1506, then bends back on itself, and then extends in a second direction away from the joint 1506 such that the first strand 1508 crosses over itself. The intersection of the first strand 1508 with itself forms the first restriction 1518 that limits movement of the second interlocking portion 1514 relative to the first interlocking portion 1512. The bent portion 1513 of the first strand 1508 (i.e., the length of the first strand 1508 between the intersecting portions of the first strand 1508) and the first restriction 1518 together enclose an opening 1522 in the first interlocking portion 1512. Although the bent portion 1513 of the first strand 1508 is shown in FIG. 15 as having a looped or curved shape, in other embodiments the bent portion 1513 may have any shape or configuration so long as the first strand 1508 changes direction along the bent portion 1513. For example, in some embodiments one or more regions of the bent portion 1513 may be generally linear.

Along the second interlocking portion 1514, the second strand 1510 extends towards the joint 1506, then bends back on itself while extending through the opening 1522 in the first interlocking portion 1513, then extends away from the joint 1506. In contrast to the embodiment shown in FIGS.

13A and 13B, the second strand 1510 of FIG. 15 does not cross over itself and does not form a restriction.

FIG. 16 shows an enlarged view of another embodiment of a joint 1606 that can be used in constructing the device 1300 or any other suitable medical device. As shown in FIG. 16, the joint 1606 comprises a first strand 1608 and a second strand 1610 having first and second interlocking portions 1612 and 1614, respectively. The first strand 1608 and the second strand 1610 may be two separate strands, or they may be different portions of a single, continuous strand. As described in greater detail below, the first and second interlocking portions 1612 and 1614 may move relative to one another at the joint 1606 to allow the expandable structure 1600 to longitudinally compress for conforming to tight bends in the vasculature. The first and second interlocking portions 1612 and 1614 also form first and second restrictions 1618 and 1620, respectively, that limit disengagement of and longitudinal displacement between the first and the second strand 1608 and 1610 at the joint 1606, provide column strength to enhance pushability, and prevent longitudinal shortening of the expandable structure beyond a predetermined length.

As shown in FIG. 16, along the first interlocking portion 1612, the first strand 1608 extends in a first direction towards the joint 1606, then bends back on itself, and then extends in a second direction away from the joint 1606. In contrast to the embodiment shown in FIGS. 13A and 13B, the first strand 1608 does not cross over itself and instead forms a pinched or narrowed portion (e.g., waist portion) that forms the first restriction 1618. A distance between opposing portions of the first strand 1608 at the pinched portion 1618 is less than a width or diameter of the second interlocking portion 1614 and/or an outer diameter of the second strand 1610 such that the pinched portion 1618 limits movement of the second interlocking portion 1614 relative to the first interlocking portion 1612. As shown in FIG. 16, the first strand 1608 may have a curved or u-shaped or c-shaped portion (i.e., the length of the first strand 1608 between the pinched portions of the first strand 1608) that partially encloses a gap 1622 in the first interlocking portion 1612. Although the curved portion 1613 of the first strand 1608 is shown in FIG. 16 as having a partially-looped or curved shape, in other embodiments the bent portion 1613 may have any shape or configuration so long as the first strand 1608 changes direction along the curved portion 1613. For example, in some embodiments one or more regions of the curved portion 1613 may be generally linear.

Along the second interlocking portion 1614, the second strand 1610 extends in a first direction towards the joint 1606, then bends back on itself, and then extends in a second direction away from the joint 1606. In contrast to the embodiment shown in FIGS. 13A and 13B, the second strand 1610 does not cross over itself and instead forms a pinched or narrowed portion (e.g., waist portion) that forms the second restriction 1620. A distance between opposing portions of the second strand 1610 at the pinched portion 1620 is less than a width or diameter of the first interlocking portion 1612 and/or an outer diameter of the first strand 1608 such that the pinched portion 1620 limits movement of the first interlocking portion 1612 relative to the second interlocking portion 1614. As shown in FIG. 16, the second strand 1610 may have a curved or u-shaped or c-shaped portion (i.e., the length of the second strand 1610 between the pinched portions of the second strand 1610) that partially encloses a gap 1624 in the second interlocking portion 1614. Although the curved portion 1615 of the second strand 1610 is shown in FIG. 16 as having a partially-looped or curved shape, in other embodiments the bent portion 1615 may have any shape or configuration so long as the second strand 1610 changes direction along the curved portion 1615. For example, in some embodiments one or more regions of the curved portion 1615 may be generally linear.

As shown in FIG. 16, the curved portion 1615 of the second strand 1610 extends through the gap 1622 in the first strand 1608 (or vice versa, i.e., the curved portion 1613 of the first strand 1608 extends through the gap 1624 in the second strand 1610). As such, the curved portion 1613 of the first strand 1608 and the curved portion 1615 of the second strand 1610 are interlocked and prevented from disengaging one another or moving longitudinally with respect to each other beyond a selected distance by the first and second restrictions 1618 and 1620.

FIG. 17 shows an enlarged view of yet another embodiment of a joint 1706 that can be used in constructing the device 1300 or any other suitable medical device. The components of the joint 1706 of FIG. 17 can be generally similar to the components of the joint 1606 of FIG. 16, except the curved portions of the first and second interlocking portions 1712 and 1714 are arranged in a slip-knot configuration. As shown in FIG. 17, the first and second interlocking portions 1712 and 1714 are intertwined, thereby allowing some longitudinal movement but with greater friction between the first and second interlocking portions 1712 and 1714 as compared to the first and second interlocking portions shown in FIGS. 13A-16.

It will be appreciated that any of the interlocking portions described herein may be combined in a single joint. For example, in some embodiments, a joint may comprise a pinched interlocking portion (e.g., first interlocking portion 1612 of FIG. 16) interlocking with an intersecting locking portion (e.g., first interlocking portion 1312 of FIG. 13). Moreover, any of the pinched interlocking portions and intersecting locking portions may be interlocked with a strand that does not form a restriction (e.g., strand 1510 of FIG. 15).

CONCLUSION

Although many of the embodiments are described above with respect to systems, devices, and methods for removing obstructions from a blood vessel, the technology is applicable to other applications and/or other approaches, such as treating hemorrhagic stroke when the device (e.g. the stent 400 or the device 1300) is configured as a flow diverter or bridging stent, and deployed across an aneurysm. Moreover, other embodiments in addition to those described herein are within the scope of the technology. Additionally, several other embodiments of the technology can have different configurations, components, or procedures than those described herein. Therefore, the disclosed technology can have other embodiments with additional elements, or the technology can have other embodiments without several of the features shown and described above with reference to FIGS. 1-17.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A medical device comprising:
an expandable tubular structure formed of an interwoven strand and configured to be positioned in a blood vessel, wherein the interwoven strand is arranged to form a plurality of cells and a plurality of joints between adjacent cells, and
wherein at least one of the joints includes a first strand slidably interlocked with a second strand, and wherein at least one of the first strand and the second strand bends back on itself to form a restriction that limits disengagement of the first strand and the second strand at the joint, and wherein:
the first strand bends back on itself to form a narrowed portion with itself, and the narrowed portion of the first strand forms a first restriction such that the second strand cannot move through the first narrowed portion, and wherein the first stand forms a curved portion that partially encloses a gap, and the second strand extends through the gap.

2. The medical device of claim 1 wherein the restriction limits longitudinally compressive disengagement of the first strand and the second strand at the joint.

3. The medical device of claim 2 wherein the first strand being interlocked with the second strand limits longitudinally expansive disengagement of the first strand and the second strand at the joint.

4. The medical device of claim 1 wherein the expandable structure is formed of a single, continuous filament such that both the first strand and the second strand are portions of the same filament.

5. The medical device of claim 1 wherein the expandable structure is formed of at least a first filament and a second filament separate from the first filament, and wherein the first strand is a portion of the first filament and the second strand is a portion of the second filament.

6. The medical device of claim 1 wherein both the first strand and the second strand bend back on themselves to form a first restriction and a second restriction at the joint, respectively.

7. The medical device of claim 1 wherein
the second strand bends back on itself without crossing over itself.

8. The medical device of claim 1 wherein:
the gap is a first gap;
the second strand bends back on itself to form a narrowed portion with itself, and the narrowed portion of the second strand forms a second restriction such that the first strand cannot move through the second narrowed portion, and wherein the second strand forms a curved portion that partially encloses a second gap;
wherein the curved portion of the second strand extends through the first gap.

9. A medical device, comprising:
an expandable tubular structure formed of interconnected strands and configured to be positioned in a blood vessel, wherein the interconnected strands are arranged to form a plurality of cells and a plurality of joints between adjacent cells,
wherein the interconnected strands include:
a plurality of first strands each having a first interlocking portion, and
a plurality of second strands each having a second interlocking portion,
wherein at least some of the joints include one of the first interlocking portions slidably coupled to one of the second interlocking portions, and wherein each of the first strand and the second strand bend back on themselves to form first and second restrictions, respectively, and
wherein (a) the first strand bends back on itself to form a narrowed portion with itself, and the narrowed portion of the first strands form a first restriction such that the second interlocking portion cannot move through the first narrowed portion, and wherein the first strand forms a curved portion that partially encloses a gap, and (b) the second stand extends through the gap;
wherein, when the expandable structure is positioned around a tight bend in a blood vessel such that a first length of the expandable structure is under tensile stress and a second length of the expandable structure is under compressive stress, the first and second interlocking portions (1) move away from one another along the length under tensile stress, and (2) move toward one another along the length under compressive stress such that the expandable structure presses outwardly against the vessel wall along the bend and conforms to the curvature of the vessel wall along the bend.

10. The medical device of claim 9 wherein the restrictions limit the movement of the interlocking portions toward each other along the length.

11. The medical device of claim 10 wherein the interlocking relationship of the first strands and the second strands at the joints limits movement of the interlocking portions away from each other along the length.

12. The medical device of claim 9 wherein
the second strand bends back on itself without crossing over itself, and wherein the bent portion of the second strand extends through the gap.

13. The medical device of claim 9 wherein: the gap is a first gap,
the second strand bends back on itself to form a narrowed portion with itself, and the narrowed portion of the second strand forms a second restriction such that the first interlocking portion cannot move through the second narrowed portion, and wherein the second strand forms a curved portion that partially encloses a second gap, and wherein the curved portion of the second strand extends through the first gap.

\* \* \* \* \*

UNITED STATES PATENT AND TRADEMARK OFFICE
CERTIFICATE OF CORRECTION

PATENT NO. : 10,278,718 B2
APPLICATION NO. : 15/173343
DATED : May 7, 2019
INVENTOR(S) : Brian Martin et al.

Page 1 of 1

It is certified that error appears in the above-identified patent and that said Letters Patent is hereby corrected as shown below:

In the Claims

In Column 27, in Claim 1, Line 42, delete "stand" and insert -- strand --, therefor.

In Column 28, in Claim 9, Line 32, delete "strands form" and insert -- strand forms --, therefor.

In Column 28, in Claim 9, Line 36, delete "stand" and insert -- strand --, therefor.

Signed and Sealed this
Sixth Day of August, 2019

Andrei Iancu
*Director of the United States Patent and Trademark Office*